(12) United States Patent
Milbrandt et al.

(10) Patent No.: US 6,866,851 B1
(45) Date of Patent: Mar. 15, 2005

(54) GFRα1-RET SPECIFIC AGONISTS AND METHODS THEREFOR

(75) Inventors: Jeffrey D. Milbrandt, St. Louis, MO (US); Robert H. Baloh, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 09/473,551

(22) Filed: Dec. 28, 1999

(51) Int. Cl.$^7$ .................... A61K 39/00; A61K 39/38; A61K 38/24; C12N 5/00; A01N 37/18

(52) U.S. Cl. .................... 424/192.1; 424/185.1; 424/184.1; 530/350; 530/399; 514/2; 435/377

(58) Field of Search .................... 424/184.1, 185.1, 424/192.1; 514/2; 530/350, 399; 435/377, 325; 536/23.51

(56) References Cited

U.S. PATENT DOCUMENTS 5,739,307 A    4/1998    Johnson, Jr. et al.

FOREIGN PATENT DOCUMENTS

| WO | WO 97/33911 AQ | 9/1997 | |
|---|---|---|---|
| WO | WO-97/33911 | * 9/1997 | ......... C07K/14/475 |

OTHER PUBLICATIONS

Skolnick et al., 2000, Tibtech, 18, pp. 34–39.*
Introduction to proteins and protein engineering, 1986, Robson and Garnier, Elsevier, p. 41.*
Jing et al. GFRa2 and GFRa3 are two new receptors for ligands of the GDNF family. J.Biol.Chem., 1997 272, 52, pp. 33111–33117.*
Worby et al. Identification and characterization of GFRa3, a novel Co–receptor belonging to the glial cell line derived neurotrophic receptor family. J.Biol.Chem, 1998 273, 6, pp. 3502–3508.*
Jing et al. GFRa2 and GFRa3 are two new receptors for ligands of the GDNF family. J.Biol.Chem., 272, 52, pp. 33111–33117.*
Worby et al. Identification and characterization of GFRa3, a novel Co–receptor belonging to the glial cell line derived neurotrophic receptor family. J.Biol.Chem, 273, 6, pp. 3502–3508.*
Enokido et al., Current Biology, vol. 8, GFRα –4 and the tyrosine kinase Ret form a functional receptor complex for persephin, pp. 1019–1022, 1998.
Gash et al., Letters To Nature, Functional Recovery In Parkinsonian Monkeys Treated with GDNF, vol. 380, pp. 252–255, Mar. 21, 1996.
Lin et al., Science, GDNF: A Glial Cell Line–Derived Neurotrophic Factor for Midbrain Dopaminergic Neurons, vol. 260, pp. 1130–1132, May 21, 1993.

Trupp et al., The Journal of Cell Biology, Peripheral Expression and Biological Activities of GDNF, a New Neurotrophic Factor for Avian and Mammalian Peripheral Neurons, vol. 130 N0. 1, pp. 137–148, Jul. 1995.
Kotzbauer et al., Letters To Nature, Neurturin, A Relative Of Glial–Cell–Line–Derived Neurotrophic Factor, vol. 384, Dec. 5, 1996.
Tomac,et al., PNAS, Effects of Cerebral Ischemia In Mice Deficient in Persephin, vol. 99, No. 14, pp. 9521–9526, Jul. 9, 2002.
Milbrandt et al., Neuron; Persephin, A Novel Neurotrophic Factor Related to GDNF and Neurturin, vol. 20, pp. 245–253, Feb. 1998.
Cohen, Proc. N.A. S.; 1990 Purification of a Nerve–Growth Promoting Protein From the Mouse Salivary Gland and Its Neuro–Cytotoxic Antiserum, pp. 302–311.
Levi–Montalcini, 1999, Annals NY Academy of Sciences Effects of Mouse Tumor Transplantation On The Nervous System, pp. 330–344.
Baloh et al., TrnR2, a Novel Receptor That Mediates Neurturin and GDNF Signaling through RET, *Neuron* 18: 793–802, 1997.
Baloh et al., GFRα3 is an orphan member of the GDNF/neuturin/persephin receptor family, *Proc. Natl. Acad. Sci., USA* 95: 5801–5806, 1998.
Birren et al., Sympathetic neuroblasts undergo a developmental switch in trophic dependence, *Development* 119: 597–610, 1993.
Bjorklund, Dopaminergic transplants in experimental parkinsonism: cellular mechanisms of graft–induced functional recovery, *Current Opinion in Neurobiology* 2: 683–689, 1992.
Burmester et al., Mutational Analysis of a Transforming Growth Factor–β Receptor Binding Site, *Growth Factors* 15: 231–242, 1998.
Burnham, Polymers for delivering peptides and proteins, *Am J Hosp Pharm* 51: 210–218, 1994.
Creedon et al., Neurturin shares receptors and signal transduction pathways with glial cell line–derived neurotrophic factor in sympathetic neurons, *Proc. Natl. Acad. Sci. US* 94: 7018–7023, 1997.
Daopin et al., Crystal Structure of Transforming Growth Factor–βB: An Unusual Fold for the Superfamily, *Science* 257: 369–373, 1992.

(List continued on next page.)

Primary Examiner—John Ulm
Assistant Examiner—Olga N. Chernyshev
(74) Attorney, Agent, or Firm—Thompson Coburn LLP

(57) ABSTRACT

Chimeric GDNF family ligands which activate a GFRα/RET are disclosed. Included are chimeras which activate GFRα1/RET but do not activate GFRα2-RET or GFRα3-RET. The chimeras are useful in providing trophic support to a mammalian cell or in producing differentiation of a mammalian cell, or both, particularly when the cell is in a patient suffering from various diseases, in particular Parkinson's Disease.

5 Claims, 12 Drawing Sheets

OTHER PUBLICATIONS

Deckwerth and Johnson, Temporal Analysis of Events Associated with Programmed Cell Death (Apoptosis) of Sympathetic Neurons Deprived of Nerve Growth Factor, *J. Cell Biol. 123*: 1207–1222, 1993.

Eigenbrot and Gerber, X–ray structure of glial cell–derived neurotrophic factor at 1.9A resolution and implications for receptor binding, *Nat. Struct. Biol. 4*: 435–438, 1997.

Friden et al., Blood–Brain Barrier Penetration and in Vivo Activity of an NGF Conjugate, *Science 259*:373–377, 1993.

Grondin and Gash, Glial cell line–derived neurotrophic factor (GDNF): a drug candidate for the treatment of Parkinson's disease, *J Neurol. 245*(11 Suppl 3): 35–42, 1998.

Hefti, Neurotrophic Factor Therapy for Nervous System Degenerative Diseases, *J. Neurobiol. 25*: 1418–1435, 1994.

Henderson et al., GDNF: A Potent Survival Factor for Motoneurons Present in Peripheral Nerve and Muscle, *Science 266*: 1062–1064, 1994.

Heuckeroth et al., Neurturin and GDNF Promote Proliferation and Survival of Enteric Neuron and Glial Progenitors in Vitro, *Dev Biol 200*: 116–29, 1998.

Jing et al., GDNF–Induced Activation of the Ret Protein Tyrosine Kinase Is Mediated by GDNFR–α, a Novel Receptor for GDNF, *Cell 85*: 1113–1124, 1996.

Jing et al., GFRα–2 and GFRα–3 Are Two New Receptors for Ligands of the GDNF Family, *J Biol. Chem. 272*: 33111–33117, 1997.

Johnson et al., Dorsal Root Ganglion Neurons Are Destroyed by Exposure in utero to Maternal Antibody to Nerve Growth Factor, *Science 210*: 916–918, 1980.

Klein et al., A GPI–linked protein that interacts with Ret to form a candidate neurturin receptor, *Nature 387*: 717–721, 1997.

Kotzbauer et al., Neurturin, a relative of glial–cell–line–derived neurotrophic factor, *Nature 384*: 467–470, 1996.

Lin et al., GDNF: A Glial Cell Line–Derived Neurotrophic Factor for Midbrain Dopaminergic Neurons, *Science 260*: 1130–1132, 1993.

Milbrandt et al., Persephin, a Novel Neurotrophic Factor Related to GDNF and Neurturin, *Neuron 20*: 245–53, 1998.

Miller and Johnson, Metabolic and Genetic Analyses of Apoptosis in Potassium/Serum–Deprived Rat Cerebellar Granule Cells, *J. Neurosci. 16*: 7487–7495, 1996.

Molloy et al., Human Furin Is a Calcium–dependent Serine Endoprotease That Recognizes the Sequence Arg–X–X–Arg and Efficiently Cleaves Anthrax Toxin Protective Antigen, *J. Biol. Chem. 267*: 16396–16402, 1992.

Muller et al., Vascular endothelial growth factor: Crystal and functional mapping of the kinase domain receptor binding site, *Proc. Natl. Acad. Sci. U.S.A. 94*: 7192–7197, 1997.

Qian et al., Binding Affinity of Transforming Growth Factor–β for Its Type II Receptor Is Determined by the C–terminal Region of the Molecule, *J. Biol. Chem. 271*: 30656–30662, 1996.

Sanicola et al., Glial cell line–derived neurotrophic factor–dependent RET activation can be mediated by two different cell–surface accessory proteins, *Proc. Natl. Acad. Sci., USA 94*: 6238–6243, 1997.

Scully and Otten, NGF: Not Just for Neurons, *Cell Biol Int 19*: 459–469, 1995.

Suvanto et al., Cloning, mRNA distribution and chromosomal localisation of the gene for glial cell line–derived neurotrophic factor receptorβ, a homologue to GDNFR–α, *Human Molecular Genetics*, 1997, vol. 6, No. 8 1267–1273.

Treanor et al., Characterizatin of a multicomponent receptor for GDNF, *Nature 382*: 80–83, 1996.

Wiesmann et al., Crystal Structure at 1.7 A Resolution of VEGF in Complex with Domain 2 of the Flt–1 Receptor, *Cell 91*: 695–704, 1997.

Worby et al., Identification and Characterization of GFRα–3, a Novel Co–receptor Belonging to the Glial Cell Line–derived Neurotrophic Receptor Family, *J Biol Chem 273*: 3502–3508, 1998.

Worby et al., Glial Cell Line–derived Neurotrophic Factor Signals through the RET Receptor and Activates Mitogen–activated Protein Kinase, *J. Biol. Chem.271*:23619–23622, 1996.

Xu et al., Characterization of Two Distinct Monoclonal Antibodies Specific for Glial Cell Line–Derived Neurotrophic Factor, *J, Neurochem. 70*: 1383–1393, 1998.

Davis et al., Enzyme–Polyethylene Glycol Adducts; Rutgers University, 169–173.

\* cited by examiner

Figure 5A
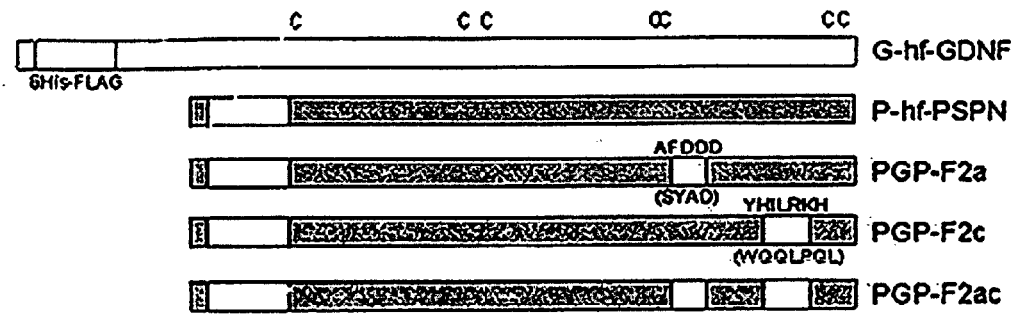
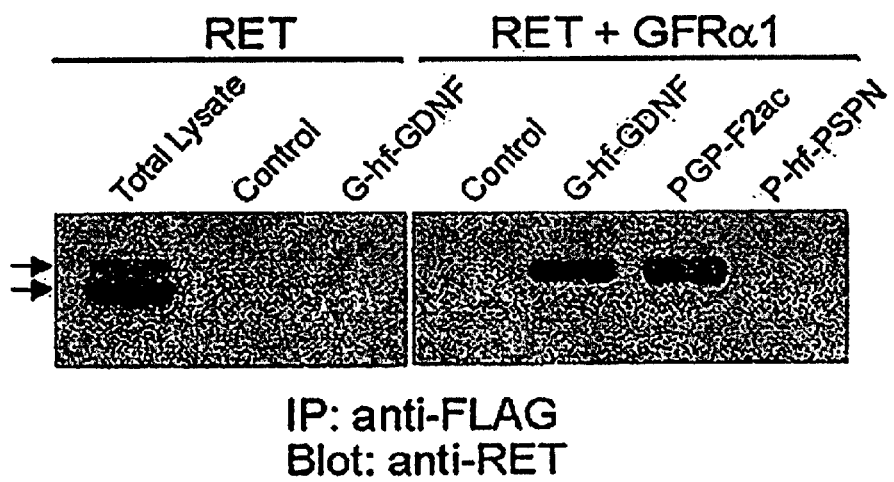
IP: anti-FLAG
Blot: anti-RET
Figure 5C

Figure 7B
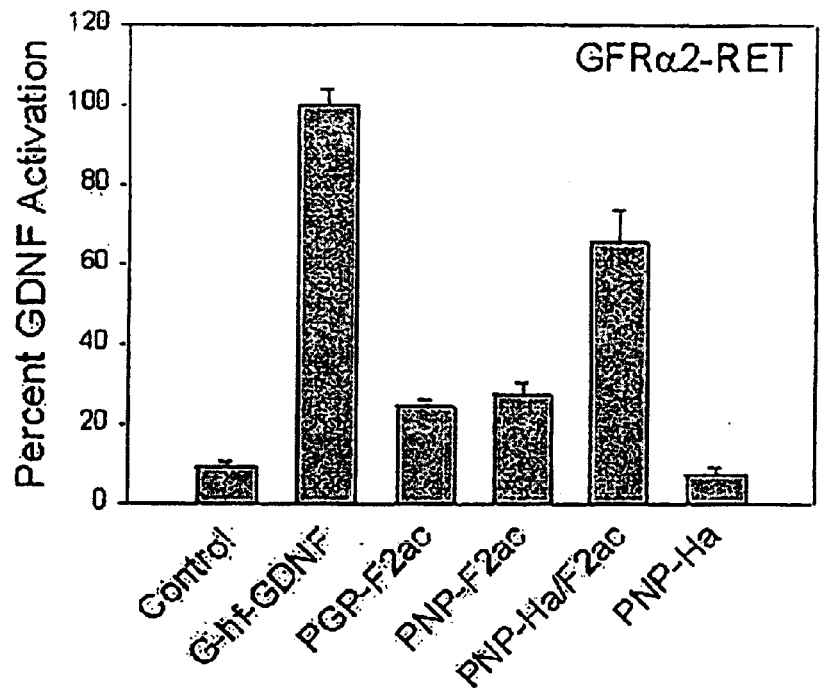
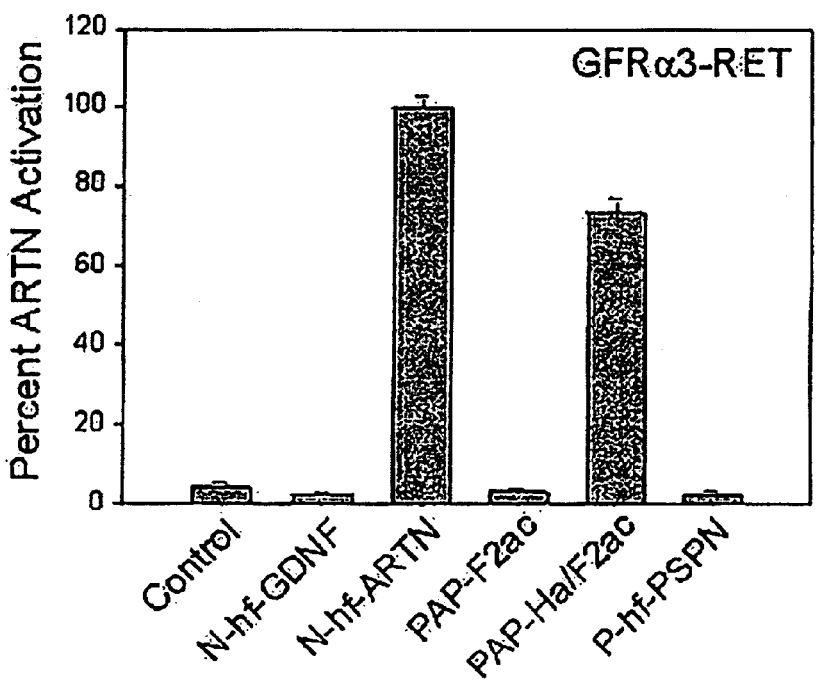
Figure 7D

GFRα1-RET SPECIFIC AGONISTS AND METHODS THEREFOR

This invention was made with Government support under National Institutes of Health/National Institute on Aging Grant No. 5R01-AG13730. The Government has certain rights in the invention.

BACKGROUND OF THE INVENTION (1) Field of the Invention

This invention relates generally to trophic or growth factors and, more particularly, to chimeric GDNF family growth factors which activate GFRα1-RET but do not substantially activate GFRα2-RET or GFRα3-RET, growth factors derived therefrom and methods therefor.

(2) Description of the Related Art

The development and maintenance of tissues in complex organisms requires precise control over the processes of cell proliferation, differentiation, survival and function. A major mechanism whereby these processes are controlled is through the actions of polypeptides known as "growth factors". These structurally diverse molecules act through specific cell surface receptors to produce these actions.

Growth factors termed "neurotrophic factors" promote differentiation, maintain a mature phenotype and provide trophic support, promoting growth, function and survival of neurons. Neurotrophic factors reside in the nervous system or in innervated tissues. Nerve growth factor (NGF) was the first neurotrophic factor to be identified and characterized (Levi-Montalcini Montalcini et al., *J. Exp. Zool.* 116: 321, 1951). NGF exists as a non-covalently bound homodimer that promotes the survival and growth of sympathetic, neural crest-derived sensory, and basal forebrain cholinergic neurons. Other effects of NGF, including effects on non-neuronal cells of the endocrine and immune systems (including inflammatory cells) are disclosed in, e.g., Levi-Montalcini and Booker, *Proc Nat'l Acad Sci* 46: 384–391, 1960; Johnson et al. *Science* 210: 916–918, 1980; Crowley et al., *Cell* 76: 1001–12, 1994; Snider and Johnson, *Ann Neurol* 26: 489–506, 1989; Hefti, *J Neurobiol* 25: 1418–35, 1994; Scully and Otten, *Cell Biol Int* 19: 459–469, 1995; Otten and Gadient, *Int. J. Devl Neurosci* 13: 147–151, 1995; and Horigome et al. *J Biol Chem* 269: 2695–2707, 1994.

In recent years it has become apparent that growth factors fall into classes, i.e. families or superfamilies based upon the similarities in their amino acid sequences. These families include, for example, the fibroblast growth factor family, the neurotrophin family and the transforming growth factor-beta (TGF-β) family. As an example of family member sequence similarities, TGF-β family members have 7 canonical framework cysteine residues which identify members of this superfamily.

The NGF family is the prototype of such a family of growth factors. Brain-derived neurotrophic factor, the second member of this family to be discovered, was shown to be related to NGF by virtue of the conservation of all six cysteines that form the three internal disulfides of the NGF monomer (Barde, *Prog Growth Factor Res* 2: 237–248, 1990 and Liebrock et al. *Nature* 341: 149–152, 1989). By utilizing the information provided by brain-derived neurotrophic factor of the highly conserved portions of two factors, additional members (NT-3, NT-4/5) of this neurotrophin family were rapidly found by several groups. (Klein, *FASEB J* 8: 738–44, 1994).

Recently, a new family of neurotrophic factors has been identified whose members are not structurally related to NGF and other neurotrophins but are structurally similar to TGF-β. As described in U.S. Pat. No. 5,739,307, and U.S. patent application Ser. Nos. 08/931,858 and 09/220,531, the known members of this subfamily of the TGF-β superfamily include glial cell line-derived neurotrophic factor (GDNF), neurturin, persephin, and artemin. The placement of GDNF, neurturin, persephin, and artemin into the same growth factor family, also referred to as the GDNF ligand family, is based on the similarities of their physical structures and biological activities. For example, human persephin has about 40% sequence identity and about 43% sequence conservation with human GDNF; about 49% sequence identity and about 50% sequence conservation with human neurturin; and about 45% sequence identity and about 48% sequence conservation with human artemin. In addition, these four proteins have the seven cysteine residues typical of TGF-β family members.

The GDNF family ligands support the survival of dopaminergic ventral midbrain neurons cultured from the embryo. Additionally, GDNF, neurturin, and persephin support the survival of spinal and facial motor neurons in both in vitro survival and in vivo injury paradigms, identifying these ligands as potential therapeutic agents in the treatment of neurodegenerative diseases (Henderson et al., *Science* 266: 1062–1064, 1994; Horger et al., *J Neurosci.* 18: 4929–37, 1998; Klein et al., *Nature* 387: 717–721, 1997; Lin et al., *Science* 260: 1130–1132, 1993; Milbrandt et al., *Neuron* 20: 245–53, 1998; Oppenheim et al., *Nature* 373: 344–346, 1995), reviewed by Grondin and Gash, *J Neurol.* 245(11 Suppl 3): 35–42, 1998). However, whereas GDNF and neurturin both support the survival of peripheral sympathetic, parasympathetic, sensory, and enteric neurons (Buj-Bello et al., *Neuron* 15: 821–828, 1995; Ebendal et al., *J Neurosci Res* 40: 276–284, 1995; Heuckeroth et al., *Dev Biol* 200: 116–29, 1998; Kotzbauer et al., *Nature* 384: 467–470, 1996; Trupp et al.,*J of Cell Biology* 130: 137–148, 1995), persephin does not support survival in any peripheral neurons tested to date (Milbrandt et al. supra).

The GDNF family ligands share receptors and signal transduction pathways (Creedon et al., *Proc. Natl. Acad. Sci. USA* 94: 7018–7023, 1997; Durbec et al., *Nature* 381: 789–793, 1996; Trupp et al., *Nature* 381: 785–789, 1996; Baloh et al., *Neuron* 18: 793–802, 1997). These proteins act through a multicomponent receptor complex in which a transmembrane signal transducing component, the Ret protein-tyrosine kinase (RET), is activated upon the binding of a growth factor of the GDNF family with a member of a family of closely related co-receptors named GFRα. A characteristic feature of the GFRα co-receptor family is that its members have no transmembrane domain and are attached to the cell surface via a glycosylphosphatidylinositol (GPI) linkage (Durbec et al., *Nature* 381: 789–793, 1996; Jing et al., *Cell* 85: 1113–1124, 1996; Treanor et al., *Nature* 382: 80–83, 1996; Trupp et al., *Nature* 381: 785–789, 1996; Baloh et al., 1997, supra). The members of the GFRα family include GFRα1 (previously known as GDNFRα, TmR1 and RetL1), GFRα2 (previously TmR2, NTNRα and RetL2), GFRα3 (previously TmR3) (GFRα Nomenclature Committee, *Neuron* 19: 485, 1997) and possibly GFRα4, a receptor currently only identified in the chicken (cGFRα4) (Enokido et al., *Current Biology* 8: 1019–1022, 1998).

Results from extensive in vitro and in vivo experimentation has established that for each GDNF family ligand there is a preferred GFRα receptor, to which the GDNF family ligand binds with highest affinity and most potently activates RET. These preferred interactions are GDNF-GFRα1, neurturin-GFRα2, and artemin-GFRα3 (Baloh et al., 1997, supra; Baloh et al., *Proc. Natl. Acad. Sci., USA* 95: 5801–5806, 1998; Jing et al., 1996, supra; Jing et al., *J Biol. Chem.* 272: 33111–33117, 1997; Klein et al., *Nature* 387: 717–721, 1997; Treanor et al., 1996, supra). Persephin does not bind or activate any of the known mammalian GFRα's but does bind to chicken GFRα4 (Milbrandt et al., supra; Baloh et al., 1998, supra, Enokido et al. supra). However, despite these preferred interactions, there is also clear cross-talk between the different ligand-receptor pairs. The known alternative interactions are neurturin-GFRAα1, artemin-GFRα1, and GDNF-GFRα2 (Baloh et al., 1998, supra; Sanicola et al., *Proc. Natl. Acad. Sci., USA* 94: 6238–6243, 1997; Suvanto et al., *Hum. Molec. Genet.* 6: 1267–1273, 1997). Thus, there is no known naturally occurring GFRα1-RET activating GDNF family ligand which does not also activate another GFRα-RET complex.

Some information is available about the roles of each GFRα receptor. Recent analysis of GFRα1-deficient mice indicated that GFRα1 is the only physiologically critical GDNF receptor in kidney organogenesis and enteric nervous system development (Cacalano et al., *Neuron* 21: 53–62, 1998; Enomoto et al., *Neuron* 21: 317–324, 1998). However, GDNF-deficient mice have greater losses in peripheral ganglia than GFRα1-deficient mice, suggesting that GDNF can utilize other receptors to support survival of peripheral neurons, likely GFRα2-RET (Cacalano et al., supra; Enomoto et al., supra). Nevertheless, several lines of evidence argue that the effects of GDNF, neurturin and artemin on dopaminergic ventral midbrain neurons are mediated through the GFRα1-RET receptor system. First, since GFRα3 is not expressed in the ventral midbrain, and artemin cannot utilize GFRα2, survival promotion of these neurons by artemin is likely through its ability to activate GFRα1-RET (Baloh et al., supra). Second, GFRα2 expression is diffuse and weak in the pars compacta region of the substantia nigra, and does not colocalize with tyrosine hydroxylase staining (TH) neurons, in contrast to the significantly stronger expression of GFRα1, which does colocalize with TH staining neurons (Horger et al., *J. Neurosci* 18: 4929–4937, 1998). Finally, the ability of both GDNF and neurturin to support the survival of dopaminergic ventral midbrain neurons is lost in GFRα1 knockout mice, indicating that at least in the embryo the survival promotion of dopaminergic ventral midbrain neurons is only through GFRα1-RET signaling (Cacalano et al., 1998).

While the in vitro interactions between the different GNDF family ligands and GFRα's is now relatively well understood, the molecular basis of this specificity and cross-talk has been heretofore unknown. The crystal structure of GDNF reveals that it is a disulfide-bonded dimer that is significantly similar to the structure of TGF-β2, as predicted by the cysteine spacing of its primary sequence (Daopin et al., *Science* 257: 369–373, 1992; Eigenbrot and Gerber, *Nat. Struct. Biol.* 4: 435438, 1997; Schlungger and Grutter, *Nature* 358: 430434, 1992). However, the structure itself yields only speculative information regarding receptor-binding surfaces. Furthermore, analogy to other TGF-β superfamily members regarding receptor-binding surfaces would likely be unfounded as the receptors used by GDNF and the TGF-β's are drastically different and likely to have little, if any, structural similarity.

It is now generally believed that neurotrophic factors regulate many aspects of neuronal function, including survival and development in fetal life, and structural integrity, function and plasticity in adulthood. Since both acute nervous system injuries as well as chronic neurodegenerative diseases are characterized by structural damage and, possibly, by disease-induced apoptosis, it is likely that neurotrophic factors play some role in these afflictions. Indeed, a considerable body of evidence suggests that neurotrophic factors may be valuable therapeutic agents for treatment of these neurodegenerative conditions, which are perhaps the most socially and economically destructive diseases now afflicting our society. For example, GDNF has been shown to relieve disease symptoms in several animal models of Parkinson's disease (reviewed by Grondin and Gash, supra). Nevertheless, because there is clear cross-talk between the different ligands and receptors, it would be desirable to have growth factors of the GDNF family which are selective for particular receptors. In particular, because there are several central and peripheral sites of GFRα2-RET or GFRα3-RET expression which could lead to side effects as a result of treatment of central nervous system injury or neurodegenerative diseases with GDNF, neurturin or artemin, there is a need for GDNF family ligand members which are more specific in activating GFRα1-RET. The identification of a GDNF family ligand which only activates GFRα1-RET, would also lead to a further elucidation of the relative roles of each GFRα receptor.

SUMMARY OF THE INVENTION

Accordingly, the inventors have succeeded in discovering that certain growth factors can be constructed which activate GFRα1-RET but which do not substantially activate GFRα2-RET or GFRα3-RET. Reference to the term "substantially" is intended to mean that the growth factor is selective for GFRα1-RET and does not activate GFRα2-RET or GFRα3-RET to an extent greater than that of persephin, which is considered to be ineffective in binding to or activating GFRα2-RET or GFRα3-RET, and/or preferably, no more than 50%, more preferably, no more than 40%, still more preferably, no more than 30% and, most preferably, no more than 20% as effective as GDNF in activating GFRα2-RET or artemin in activating GFRα3-RET.

Thus, in one embodiment, the present invention is directed to growth factors which activate GFRα1-RET but do not substantially activate GFRα2-RET or GFRα3-RET. Such growth factors can be chimeric GDNF family ligands or derivatives thereof. The derivatives can be peptidyl derivatives or non-peptidyl derivatives. Preferred peptidyl derivatives are GDNF family growth factors having conservative amino acid substitutions. In certain aspects of this embodiment, the growth factor can be based upon persephin which does not act upon GFRα1-RET. The chimeric growth factor, thus, preferably comprises a substituted persephin having different amino acids in the F2a and/or F2c regions than those in a naturally occurring persephin. F2 represents the finger 2 stretch of amino acids as determined for GDNF (Eigenbrot and Gerber, 1997, supra) and the F2a and F2c regions are portions of finger 2 as shown in FIG. 1.

The F2a region of the substituted persephin preferably comprises from one to eight amino acids identical to region F2a of GDNF, neurturin or artemin, i.e. from one to eight amino acids can be the same and in the same position in the F2a region of the substituted persephin as in the F2a region of GDNF, neurturin or artemin. Alternatively, the amino acid in a particular position in the F2a region of the substituted persephin can be a conservative amino acid substitution for the amino acid in that position in the F2a region of GDNF; neurturin or artemin. Persephin lacks an amino acid between position 71 and 72 which is present in the aligned F2a regions of GDNF and neurturin and, hence, reference to amino acid substitutions in the F2a region of persephin is intended to include an insertion between positions 71 and 72 with an amino acid in that aligned position from GDNF, neurturin or artemin or a conservative amino acid substitution therefor.

Additionally, the F2c region of the substituted persephin of this embodiment preferably comprises from one to eight amino acids identical to region F2c of GDNF, neurturin or artemin, i.e. from one to eight amino acids can be the same and in the same position in the F2c region of the substituted persephin as in the F2c region of GDNF, neurturin or artemin. Alternatively, the amino acid in a particular position in the F2c region of the substituted persephin can be a conservative amino acid substitution for the amino acid in that position in the F2c region of GDNF, neurturin or artemin.

Preferably, the growth factor of the present invention comprises a substituted human persephin (SEQ ID NO:1), mouse persephin (SEQ ID NO:2) or rat persephin (SEQ ID NO:3) having substitutions in the F2a and/or F2c regions. The persephin sequence can also include variations of these persephin sequences, having conservative amino acid substitutions outside of the F2a and F2c regions. The F2a and F2c regions in the substituted persephin sequences have amino acids substitutions from the F2a and F2c regions of human GDNF (SEQ ID NO:4), mouse GDNF (SEQ ID NO:5), rat GDNF (SEQ ID NO:6), human neurturin (SEQ ID NO:7), mouse neurturin (SEQ ID NO:8), human artemin (SEQ ID NO:9), mouse artemin (SEQ ID NO:10). Preferably, the growth factor of the present invention comprises a substituted human persephin having F2a and F2c region substitutions independently selected from corresponding regions of human GDNF, human neurturin or human artemin. More preferably, the growth factor comprises SEQ ID NO:23, SEQ ID NO:24 or SEQ ID NO:25; the most preferred growth factor consists of SEQ ID NO:26, SEQ ID NO:27 or SEQ ID NO:28.

The present invention also includes compositions comprising a pharmaceutically acceptable preparation of the GFRα1-RET selective growth factors of the present invention.

In another embodiment, the present invention is directed to a nucleic acid comprising a polynucleotide encoding a growth factor which activates GFRα1-RET but does not substantially activate GFRα2-RET or GFRα3-RET. The encoded growth factor is preferably a chimeric GDNF family ligand or a conservatively substituted derivative thereof. The encoded chimeric growth factor, preferably, comprises a persephin having the F2a and/or F2c region substituted with from one to eight amino acids identical to and in the same position as the amino acid in the F2a region or F2c region, respectively, of GDNF, neurturin or artemin. Alternatively, the encoded F2a region or F2c region amino acid substitutions can comprise a conservative amino acid substitution for the amino acid in that position in the F2a region or F2c region of GDNF, neurturin or artemin. Preferably, the encoded, substituted persephin is a substituted human persephin (SEQ ID NO:1), mouse persephin (SEQ ID NO:2) or rat persephin (SEQ ID NO:3) having amino acid substitutions in the F2a and/or F2c regions. The encoded persephin sequence can also include variations of these persephin sequences, having conservative amino acid substitutions outside of the F2a and F2c regions. The F2a and F2c regions in the encoded chimeric persephin sequences have amino acid substitutions from the F2a and F2c regions of human GDNF (SEQ ID NO:4), mouse GDNF (SEQ ID NO:5), rat GDNF (SEQ ID NO:6), human neurturin (SEQ ID NO:7), mouse neurturin (SEQ ID NO:8), human artemin (SEQ ID NO:9), or mouse artemin (SEQ ID NO:10). Preferably, the encoded sequence comprises a substituted human persephin having F2a and F2c region substitutions independently selected from corresponding sequences of human GDNF, human neurturin or human artemin. More preferably, the encoded sequence comprises SEQ ID NO:23, SEQ ID NO:24 or SEQ ID NO:25; the most preferred encoded growth factor consists of SEQ ID NO:26, SEQ ID NO:27 or SEQ ID NO:28.

In another embodiment, the present invention comprises a vector which comprises expression regulatory elements operably linked to a polynucleotide which encodes a growth factor which activates GFRα1-RET but does not substantially activate GFRα2-RET or GFRα3-RET and which is, preferably, a chimeric GDNF family ligand. The present invention also encompasses a host cell which is transformed with the vector.

In an additional embodiment, the present invention provides chimeric GDNF family ligands with an altered N-terminus. The N-terminus can be eliminated, truncated, or substituted with the N-terminus of another GDNF family member or another protein such as a member of another TGF-β superfamily member. These chimeras retain the GFRα-RET activating ability of the GDNF family ligand.

The growth factors of the present invention can be used to provide trophic support or produce differentiation in a mammalian cell. Thus, in another embodiment, the present invention comprises a method for providing trophic support to a mammalian cell or for producing differentiation of a mammalian cell or both. The method comprises treating the cell with an effective amount of a growth factor which activates GFRα1-RET but does not substantially activate GFRα2-RET or GFRα3-RET. The growth factor is preferably a chimeric GDNF family ligand or a conservatively substituted derivative thereof. The chimeric growth factor, preferably, comprises a persephin having the F2a region and/or F2c region substituted with from one to eight amino acids identical to and in the same position as that amino acid in the F2a region or F2c region, respectively, of GDNF, neurturin or artemin. Alternatively, the F2a region or F2c region amino acid substitutions can comprise a conservative amino acid substitution for the amino acid in that position in the F2a region or F2c region of a GDNF, neurturin or artemin. Preferably, the substituted persephin is a substituted human persephin (SEQ ID NO:1), mouse persephin (SEQ ID NO:2) or rat persephin (SEQ ID NO:3) having amino acid substitutions in the F2a and/or F2c regions. The persephin sequence can also include variations of these persephin sequences, having conservative amino acid substitutions outside of the F2a and F2c regions. The F2a and F2c regions in the substituted or chimeric persephin sequences preferably have amino acid substitutions from the F2a and F2c regions of human GDNF (SEQ ID NO:4), mouse GDNF (SEQ ID NO:5), rat GDNF (SEQ ID NO:6), human neurturin (SEQ ID NO:7), mouse neurturin (SEQ ID NO:8), human artemin (SEQ ID NO:9), or mouse artemin (SEQ ID NO:10). Preferably, the growth factor of the present invention comprises a substituted human persephin having F2a and F2c region substitutions independently selected from corresponding regions of human GDNF, human neurturin or human artemin. More preferably, the growth factor comprises SEQ ID NO:23, SEQ ID NO:24 or SEQ ID NO:25; the most preferred growth factor consists of SEQ ID NO:26, SEQ ID NO:27 or SEQ ID NO:28. The mammalian cell can be any cell which contains GFRα1-RET, preferably, a neuronal cell, a hematopoietic cell or a cardiac muscle cell.

The treatment can further comprise administering to the cell a GFRα1 polypeptide.

In a variation of this embodiment, the cell can be treated with a nucleic acid comprising a polynucleotide which encodes for expression, a growth factor which activates GFRα1-RET but does not substantially activate GFRα2-RET or GFRα3-RET. The encoded growth factor is preferably a chimeric GDNF family ligand or a conservatively substituted derivative thereof. In addition the cell can also be treated with a GFRα1 polypeptide or a polynucleotide encoding a GFRα1 polypeptide.

In one aspect of this embodiment, the cell can be in an patient and the treatment comprises administering the growth factor to the patient. The method also encompasses administering a polynucleotide encoding the growth factor to the patient or implanting into the patient a cell which expresses the growth factor. The cell can be a neuronal cell in a patient suffering from peripheral neuropathy, amyotrophic lateral sclerosis, Alzheimer's disease, Parkinson's disease, Huntington's disease, diabetes, AIDS, ischemic stroke, acute brain injury, acute spinal cord injury, a nervous system tumor such as neuroblastoma, multiple sclerosis, infection, side effects of chemotherapy, or an enteric disease such as idiopathic constipation or constipation associated with Parkinson's disease, spinal cord injury or use of opiate pain-killers. The cell can also be a non-neuronal cell such as, for example, in a patient suffering from small cell lung carcinoma. The cell can also be a hematopoietic cell in a patient suffering from eosinopenia, basopenia, lymphopenia, monocytopenia, neutropenia, anemia, thrombocytopenia; or stem-cell insufficiency or a cardiac muscle cell in a patient suffering from cardiomyopathy or congestive heart failure.

In another embodiment, the present invention comprises a method for preventing or treating cellular degeneration or insufficiency in an individual. The method comprises administering to the individual a therapeutically effective amount of a growth factor which activates GFRα1-RET but does not substantially activate GFRα2-RET or GFRα3-RET. The growth factor is preferably, a chimeric GDNF family ligand or a conservatively substituted derivative thereof. The chimeric growth factor, preferably, comprises a persephin having the F2a region and/or F2c regions independently substituted with from one to eight amino acids identical to and in the same position as that amino acid in the F2a region or F2c region, respectively, of GDNF, neurturin or artemin. Alternatively, the F2a region or F2c region amino acid substitutions can comprise a conservative amino acid substitution for the amino acid in that position in the F2a region or F2c region of GDNF, neurturin or artemin. Preferably, the substituted persephin is a substituted human persephin (SEQ ID NO:1), mouse persephin (SEQ ID NO:2) or rat persephin (SEQ ID NO:3) having amino acid substitutions in the F2a and/or F2c regions. The persephin sequence can also include variations of these persephin sequences, having conservative amino acid substitutions outside of the F2a and F2c regions. The F2a and F2c regions in the substituted or chimeric persephin sequences preferably have amino acid substitutions from the F2a and F2c regions of human GDNF (SEQ ID NO:4), mouse GDNF (SEQ ID NO:5), rat GDNF (SEQ ID NO:6), human neurturin (SEQ ID NO:7), mouse neurturin (SEQ ID NO:8), human artemin (SEQ ID NO:9), or mouse artemin (SEQ ID NO:10). Preferably, the growth factor comprises a substituted human persephin having F2a and F2c region substitutions independently selected from corresponding regions of human GDNF, human neurturin or human artemin. More preferably, the growth factor comprises SEQ ID NO:23, SEQ ID NO:24 or SEQ ID NO:25; the most preferred growth factor consists of SEQ ID NO:26, SEQ ID NO:27 or SEQ ID NO:28. The mammalian cell can be any cell which contains GFRα1-RET, preferably, a neuronal cell, a hematopoietic cell or a cardiac muscle cell. The treatment can further comprise administering to the individual a GFRα1 polypeptide.

In a variation of this method, a polynucleotide encoding the growth factor can be administered to the individual. Moreover, a cell which expresses the growth factor can be implanted into the individual. In addition, the treatment with the growth factor can be facilitated by also administering to the individual a GFRα1 polypeptide or a polynucleotide encoding a GFRα1 polypeptide or a cell which expresses a GFRα1 polypeptide can be implanted into the individual.

The growth factor or polynucleotide encoding the growth factor can be administered to an individual suffering from (a) neuronal degeneration resulting from peripheral neuropathy, amyotrophic lateral sclerosis, Alzheimer's disease, Parkinson's disease, Huntington's disease, diabetes, AIDS, ischemic stroke, acute brain injury, acute spinal cord injury, a nervous system tumor such as neuroblastomas, multiple sclerosis, infection, chemotherapy side effects, or an enteric disease such as idiopathic constipation or constipation associated with Parkinson's disease, spinal cord injury or use of opiate pain-killers, (b) from small cell lung carcinoma, (c) from hematopoietic cell degeneration or insufficiency resulting from eosinopenia, basopenia, lymphopenia, monocytopenia, neutropenia, anemia, thrombocytopenia, or stem-cell insufficiencies therefor, or (d) cardiac muscle degeneration or insufficiency resulting from cardiomyopathy or congestive heart failure.

In an additional embodiment, mimics of neurturin are provided which activate GFRα1-RET and GFRα2-RET but do not substantially activate GFRα3-RET. These mimics comprise persephin having amino acid substitutions in regions Ha, F2a and F2c from neurturin, or conservative amino acid substitutions therefor. Nucleic acids comprising polynucleotides encoding these mimics are also provided. These mimics can substitute for neurturin, for example in methods for providing trophic support to a mammalian cell or producing differentiation of a mammalian cell, or in methods for preventing or treating cellular degeneration or insufficiency in an individual. Similarly, mimics of artemin are also provided which activate GFRα1-RET and GFRα3-RET but do not substantially activate GFRα2-RET. These mimics comprise persephin having amino acid substitutions in regions Ha, F2a and F2c from artemin, or conservative amino acid substitutions therefor. Nucleic acids comprising polynucleotides encoding these mimics are also provided. These mimics can substitute for artemin, for example in methods for providing trophic support to a mammalian cell or producing differentiation of a mammalian cell, or in methods for preventing or treating cellular degeneration or insufficiency in an individual.

Among the several advantages achieved by the present invention, therefore, may be noted the provision of chimeric GDNF family ligands, which can be used to prevent the atrophy, degeneration or death of certain cells, in particular, neurons in need of trophic support; the provision of polynucleotides encoding chimeric GDNF family ligands for use in gene therapy; the provision of methods for obtaining chimeric GDNF family ligands by recombinant techniques; the provision of methods for providing trophic support to target cells, particularly neurons; and the provision of methods for treating disease conditions involving cellular degeneration, and in particular, neuronal dysfunction and degeneration.

BRIEF DESCRIPTION OF THE DRAWINGS

FIG. 5A is a schematic representation of G-hf-GNDF, P-hf-PSPN, and GDNF/persephin replacement chimeras (PGP) for gain-of-function analysis, where the persephin amino acid sequence in parentheses below the schematics was replaced by the GDNF sequence shown above;

FIG. 5C is an image of a RET immunoblot of anti-FLAG®-immunoprecipitated lysate from neuro2a cells either untransfected (RET) or transfected with FLAG®-tagged GFRα1 (RET+GFRα1) treated with the indicated factor at 25 ng/mL, where a fraction of the total lysate shows a RET doublet, with the upper band corresponding to the mature cell-surface form;

FIG. 7B is a graph showing the ability of inability of the six molecules depicted in FIG. 7A to activate GFRα2-RET;

FIG. 7D is a graph showing the ability of inability of the five molecules depicted in FIG. 7C to activate GFRα3-RET;

DESCRIPTION OF THE PREFERRED EMBODIMENTS

The present invention is directed to growth factors which selectively activate GFRα1-RET without substantially activating GFRα2-RET or GFRα3-RET. Such growth factors are, preferably, chimeric GDNF family ligand growth factors which have the ability to activate a GFRα1-RET complex, and are thus useful for promoting the survival of peripheral and central neuronal populations in vivo or in vitro.

Figure 1:
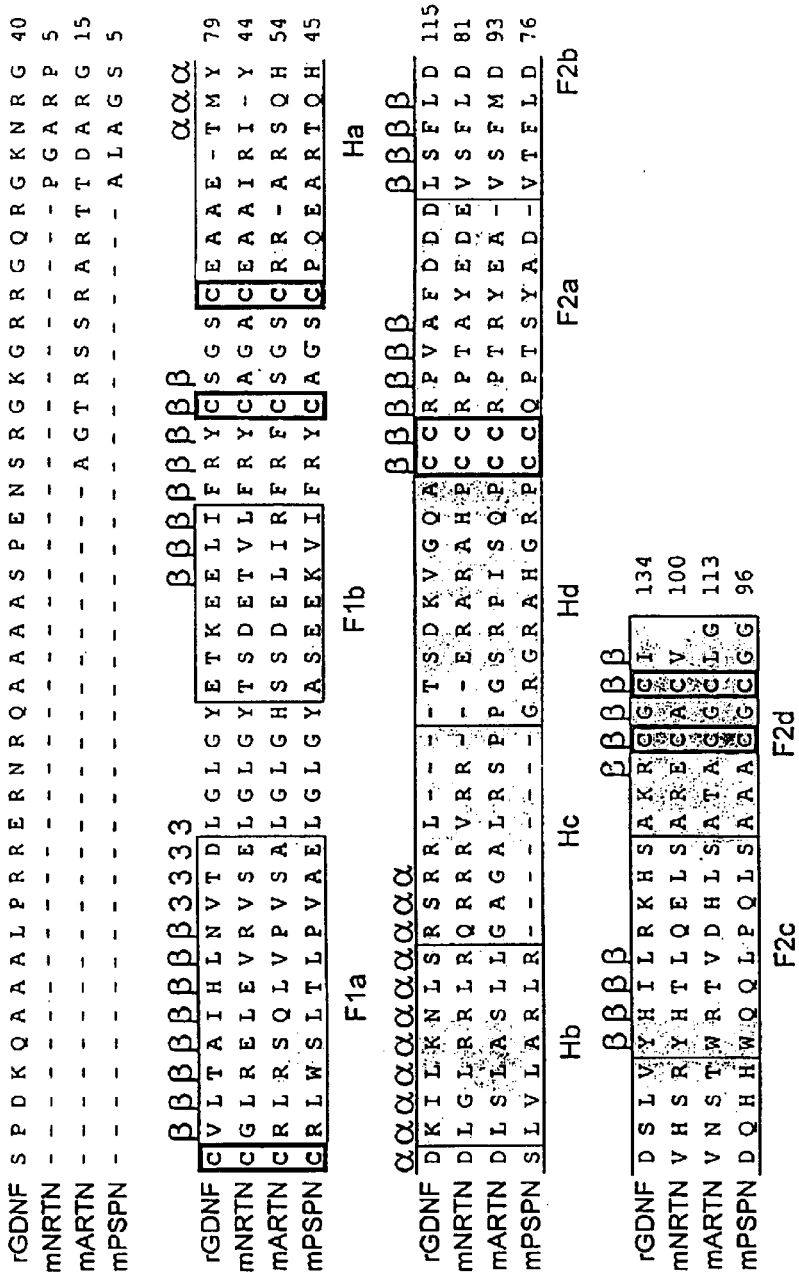
FIG. 1 illustrates the amino acid sequence alignment of rat GDNF (comprising SEQ ID NO:6); mouse neurturin (comprising SEQ ID NO:8); mouse artemin (comprising SEQ ID NO:10); and mouse persephin (comprising SEQ ID NO:2), where the sequences include the region N-terminal to the first canonical cysteine and C-terminal to the seventh canonical cysteine, where the canonical cysteines are indicated by a thick outline, and where secondary structure elements ('α' for α-helix, 'β' for β-strand and '3' for $3_{10}$-helix) as determined for GDNF (Eigenbrot and Gerber, Nat. Strucl. Biol. 4: 435–438, 1997) are indicated above the alignment and the regions delineated for homologue-scanning mutagenesis are in gray blocks, with the name of the region (F1a–F1b for finger 1, Ha–Hd for heel, F2a–F2d for finger 2) is below the given region.

In one embodiment, the present invention provides novel chimeras which vary from the previously known naturally occurring GDNF ligand family members GDNF, artemin, neurturin, and persephin by their ability to activate mammalian GFRα1-RET without substantially activating GFRα2-RET or GFRα3-RET complexes. Examples of these novel chimeras are PGP-F2ac (e.g., SEQ ID NOS:12, 23, and 26), PNP-F2ac (e.g., SEQ ID NOS:14, 24, and 27), and PAP-F2ac (e.g., SEQ ID NOS:16, 25, and 28), in which the sequences are identical to human persephin (e.g., SEQ ID NO:1), mouse persephin (SEQ ID NO:2), or rat persephin (SEQ ID NO:3) except that amino acids 63–66 in the F2a region and/or amino acids 76–82 in the F2c region (corresponding to amino acids 68–71 and 81–87 of full length persephin, as depicted in FIG. 1) are replaced with the corresponding amino acids from a GDNF in PGP-F2ac, a neurturin in PNP-F2ac, or an artemin in PAP-F2ac. Although persephin sequences do not bind to or activate GFRα1-RET, GFRα2-RET or GFRα3-RET, the replacement of these amino acids of persephin with amino acids in the same aligned positions from GDNF, neurturin, or artemin, confers upon the chimeric molecule the ability to bind to and activate GFRα1-RET. However, even though the persephin amino acids 63–66 and 76–82 are substituted with regions from growth factors which can also activate GFRα2-RET (neurturin and GDNF) and GFRα3-RET (artemin), the chimeras do not activate those receptors.

As used herein, the ability to substantially activate a GFRα-RET complex by a GDNF family ligand is defined as the ability of that ligand to activate the MAP kinase pathway at a level preferably at least about 40%, more preferably at least about 50%, and most preferably at least about 80% of the ability of GDNF to activate that pathway through GFRα1-RET activation. This can be measured, e.g., by measuring luciferase activity after activating RET-expressing cells transformed with expression plasmids encoding the individual GFRα receptor together with the Gal4-Elk/Gal4-Luc reporter system as previously described with GDNF (Worby et al., *J Biol Chem* 273: 3502–3508, 1998; Worby et al., *J. Biol. Chem.* 271:23619–23622, 1996).

As used herein, regions in other GDNF family ligands which are "corresponding" or "analogous" to persephin amino acids 65–71 (also known as the F2a region—FIG. 1) and 81–87 (the F2c region), starting at the first canonical cysteine, are meant to encompass the regions of those growth factors which are aligned with those persephin regions by commonly used alignment methods which are designed to align regions according to similar predicted tertiary structures. An example is the Clustal method (Higgins et al, *Cabios* 8:189–191, 1992) of multiple sequence alignment in the Lasergene biocomputing software (DNASTAR, INC, Madison, Wis.). In this method, multiple alignments are carried out in a progressive manner, in which larger and larger alignment groups are assembled using similarity scores calculated from a series of pairwise alignments. Optimal sequence alignments are obtained by finding the maximum alignment score, which is the average of all scores between the separate residues in the alignment, determined from a residue weight table representing the probability of a given amino acid change occurring in two related proteins over a given evolutionary interval. Penalties for opening and lengthening gaps in the alignment contribute to the score. The default parameters used with this program are as follows: gap penalty for multiple alignment=10; gap length penalty for multiple alignment=10; k-tuple value in pairwise alignment=1; gap penalty in pairwise alignment=3; window value in pairwise alignment=5; diagonals saved in pairwise alignment=5. The residue weight table used for that alignment program is PAM250 (Dayhoff et al., in *Atlas of Protein Sequence and Structure*, Dayhoff, Ed., NBRF, Washington, Vol. 5, suppl. 3, p. 345, 1978).

When the GDNF family ligands are aligned using the Clustal method (see, e.g., FIG. 1), the F2a and F2c regions consist of amino acids 60–66 and 76–83 of persephin, starting at the first canonical cysteine residue (as set forth in SEQ ID NOS:1–3). When numbered from the N-terminus of persephin, as depicted in FIG. 1, these regions correspond to amino acids 65–71 and 81–88, respectively. When persephin is aligned by the Clustal method with GDNF, the F2a and F2c regions correspond to amino acids 63–71 and 80–87, respectively, of GDNF as set forth in SEQ ID NOS:4–6 and amino acids 103–110 and 120–127, respectively, of full length GDNF (FIG. 1), and have the sequences RPIAFDDD and YHILRKHS, respectively, in human GDNF (SEQ ID NO:4). In neurturin, F2a and F2c are amino acids 64–71 and 81–88, respectively, in SEQ ID NOS:7 and 8, and amino acids 69–76 and 86–93, respectively, of full length neurturin (FIG. 1), and have the sequences RPTAYEDE and YHTVHELS in human neurturin (SEQ ID NO:7). In artemin, F2a and F2c are amino acids 67–73 and 83–90, respectively, in SEQ ID NOS:9 and 10, and amino acids 82–88 and 98–105, respectively, of full length artemin (FIG. 1), and have the sequences RPTRYEA and WRTVDRLS in human artemin (SEQ ID NO:9).

The seven amino acids 60–66 of the persephin F2a region correspond to the eight amino acids 63–70 of GDNF or 64–71 of neurturin because Clustal analysis creates a gap between amino acid 66 and 67 in persephin when aligned with GDNF or neurturin (see, e.g., FIG. 1). Thus, the eighth amino acid in this region from GDNF or neurturin is not present in persephin (and artemin).

As it is believed that the replacement of amino acids 60–66 and 76–83 of any persephin (as numbered in SEQ ID NOS:1–3), now known or unknown, with analogous regions from any GFRα1-RET activating GDNF family ligand (now known or unknown) would create a growth factor which activates GFRα1-RET without activating GFRα2-RET or GFRα3-RET, the scope of this embodiment is not meant to be limited to the GDNP family members disclosed herein, but is meant to encompass any GDNF family member. The invention also encompasses chimeras wherein the persephin is from one species and each substituting amino acid within 60–66 and 76–83 can be that of the same or different species.

It is also believed that the chimeras need not comprise the exact aminoacid sequence of the GDNF family ligand from which they were derived in order to retain the ability to activate GFRα1-RET. Rather, conservative substitutions in the chimeras are within the scope of the present invention. Conservative amino acid substitutions refer to the interchangeability of residues having similar side chains. Conservatively substituted amino acids can be grouped according to the chemical properties of their side chains. For example, one grouping of amino acids includes those amino acids have neutral and hydrophobic side chains (A, V, L, I, P, W, F, and M); another grouping is those amino acids having neutral and polar side chains (G, S, T, Y, C, N, and Q); another grouping is those amino acids having basic side chains (K, R, and H); another grouping is those amino acids having acidic side chains (D and E); another grouping is those amino acids having aliphatic side chains (G, A, V, L, and I); another grouping is those amino acids having aliphatic-hydroxyl side chains (S and T); another grouping is those amino acids having aminecontaining side chains (N, Q, K, R, and H); another grouping is those amino acids having aromatic side chains (F, Y, and W); and another grouping is those amino acids having sulfur-containing side chains (C and M). Preferred conservative amino acid substitutions groups are: R-K; E-D, Y-F, L-M; V-I, and Q-H.

As used herein, the chimeras of the present invention can also include modifications of the sequences identified herein, including sequences in which one or more amino acids have been inserted, deleted or replaced with a different amino acid or a modified or unusual amino acid, as well as modifications such as glycosylation or phosphorylation of one or more amino acids so long as the chimera containing the modified sequence retains the ability to activate GFRα1-RET. Amino acid(s) can be added to or removed from the N-terminus, C-terminus or within the amino acid sequence, provided the structural Cys residues are retained, which are believed to be required for GFRA-RET activating activity. Thus, the sequences set forth in SEQ ID NOS:1–10, which are sequences only between the first and seventh canonical cysteines of the GDNF family members, are believed to be the minimum length required for activity of these growth factors.

It is also known that the substitution of persephin amino acids with amino acids from a GFRα1-RET activating growth factor need not encompass all of amino acids 60–66 and 76–83 (numbering of SEQ ID NOS:1–3). For example, the GFRα1-RET activating chimeras PGP-F2ac, PNP-F2ac, and PAP-F2ac all comprise only the substitution of F2a amino acid residues 63–66 and F2c amino acid residues 76–82 (residue 83 is an S in all known GDNF family members). Additionally, a comparison of the GDNF, neurturin, and artemin amino acids in these regions with the corresponding amino acids of persephin reveals that the only GDNF, neurturin, and artemin amino acids which do not also occur in persephin are those at position 65, 77, 78, 80, and 81, as well as the amino acid which is "missing" between amino acid 66 and 67 in persephin. The "missing" amino acid between 66 and 67 is a D in known GDNF sequences and an E in known neurturin, which are both acidic amino acids. However, this amino acid is also missing in artemin which activates GFRα1. Therefore the provision of that missing amino acid in a persephin chimera is unlikely to influence the ability of the chimera to activate GFRα1. At position 65, the known persephins have an A or a T, which are both uncharged at physiological pH, whereas the GFRα1-activating growth factors have an E or a D, which are both acidic. At position 77, the persephins have a Q, which is uncharged and polar, whereas known GFRα1-RET activating growth factors have an R or an H, which are basic. At position 78, the persephins have a Q (uncharged and polar) or an R (basic), whereas the GFRα1-RET activating growth factors have a T (uncharged and polar) or an I (nonpolar). At position 80, the persephins have P (nonpolar), whereas the GFRα1-RET activating growth factors have D, H, (both acidic), R (basic), and Q (uncharged and polar). Finally, at position 81, the persephins have a Q (uncharged and polar), whereas the GFRα1-RET activating growth factors have an H (basic), an E (acidic), or a K (basic). Based on this analysis, only the substitutions at residues 65 and 77 represent an unequivocal change to a particular charge or polarity from the "nonfunctional" (i.e., does not activate GFRα1-RET) persephin to the "functional" (GFRα1-RET activating) GDNF family ligands. Therefore, these "hot spots" may be particularly important for GFRα1-RET activation. Thus, it is believed that GFRα1-RET activation can be achieved with a persephin wherein (a) from 1 to 4of amino acids 63–66 are substituted with the corresponding amino acids of a GFRα1-RET activating GDNF family ligand, or a conservatively substituted variant thereof, including at least the substitution of amino acid 65 with an acidic amino acid; and (b) from 1 to 7 of amino acids 76–82 are substituted with the corresponding amino acids of a GFRα1-RET activating GDNF family ligand, or a conservatively substituted variant thereof, including the substitution of amino acid 77 with a basic amino acid. Preferred substitutions at position 65 are E and D. Preferred substitutions at position 77 are K, R, or H; most preferred are R and H.

In another embodiment, the present invention provides chimeric GDNF family ligands comprising a persephin wherein all three of the F2a, the F2c, and the Ha regions are substituted with the equivalent regions of a GFRα-RET activating GDNF family ligand. The Ha region encompasses amino acids 33–41 of persephin SEQ ID NOS:1–3 (equivalent to amino acids 38–46 of full length persephin—FIG. 1) and equivalent regions (as determined by Clustal analysis) of other GDNF family ligands (FIG. 1). The addition of the Ha region provides the ability to activate GFRα2-RET or GFRα3-RET, depending on the source of the Ha region. If the Ha region (along with F2a and F2c) is derived from neurturin (e.g., PNP-Ha/F2ac—FIG. 7A), the chimera will activate GFRα2-RET; if the Ha region (along with F2a and F2c) is derived from artemin (e.g., PAP-Ha/F2ac—FIG. 7C) the chimera will activate GFRα3-RET. It has been found that the activation of GFRα2-RET or GFRα3-RET by these chimeras is generally about 70% of the activation of that GFRα-RET by the natural (e.g., neurturin or artemin) ligand (see, e.g., FIG. 7). Because neurturin does not substantially bind to or activate GFRα3, chimeras such as PNP-Ha/F2ac would be expected to activate only GFRα1-RET and GFRα2-RET and not GFRα3-RET or other GFRα-RET complexes having similar additional binding and activation requirements. Similarly, because artemin does not substantially bind to or activate GFRα2-RET, chimeras such as PAP-Ha/2ac would be expected to activate only GFRα1-RET and GFRα3-RET and not GFRα2-RET or other GFRα-RET complexes having similar additional binding and activation requirements.

PNP-Ha/F2ac and PAP-Ha/F2ac thus represent mimics of neurturin and artemin, respectively. As used herein, a mimic of a GDNF family ligand is a chimera which activates the same GFRα-RET receptor as the GDNF family ligand but which primarily comprises a different GDNF family ligand. Because mimics such as PNP-Ha/F2ac and PAP-Ha/F2ac activate the same GFRα-RET receptors as neurturin and artemin, respectively, it is believed that they can substitute for those GDNF family ligands in any treatment regime, such as described in U.S. Pat. No. 5,843,914 for neurturin, or U.S. patent application Ser. No. 09/218,698 for artemin, both of which are hereby incorporated by reference.

As with the persephin chimeras having only the F2a and F2c regions from GFRα1-RET activating ligands, the persephin chimeras with the F2a, F2c, and Ha chimeric regions can encompass conservatively substituted and modified amino acids. The chimeric regions from the GFRα1-RET activating ligands can also comprise only partial substitutions, as previously discussed.

In an additional embodiment, the present invention provides chimeric GDNF family ligands with an altered N-terminal region. It has been discovered that the region N-terminal to the first cysteine residue is not necessary to activate a GFRα/RET (see Example 1). Thus, any GDNF family ligand with an N-terminal region from any other GDNF family ligand, or with any other sequence of about 100 amino acids or less (including a lack of an N-terminal region) would be expected to activate the GFRα-RET which the wild-type ligand activates. Thus, this embodiment comprises a GDNF family member with from zero to 100 amino acids N-terminal to the first cysteine residue. This N-terminal region can comprise a functional sequence, such as a signal sequence or a prepro region comprising a signal sequence. It is well known in the art that many proteins are synthesized within a cell with a signal sequence at the N-terminus of the mature protein sequence and the protein carrying such a leader sequence is referred to as a preprotein. The pre region can serve as a signal peptide which directs transport of the protein to subcellular organelles or outside of the cell. The pre-portion of the protein is cleaved during cellular processing of the protein. In addition to a pre-leader sequence, many proteins contain a distinct pro sequence that describes a region on a protein that is a stable precursor of the mature protein. In view of the processing events known to occur with other TGF-β family members, the inventors believe that the form of the GDNF family ligands which are synthesized within a cell is the pre-pro-ligand. The GDNF family ligand pre-region is thus generally followed by a pro-domain which is believed to preferably terminate with an RXXR consensus site immediately before the N-terminal amino acid of the mature ligand. Proteins synthesized with both pre- and pro-regions are referred to as preproproteins.

Thus, within the scope of the present invention are GDNF family ligands containing a pre-pro-region from another GDNF family ligand or another protein, as well as polynucleotides encoding such polypeptides. The polypeptides can generate a mature ligand upon cleavage of the pre-pro-region and the polynucleotides can be used in an expression system to produce the polypeptide which upon cleavage of the non-artemin pre-pro-region yields mature artemin. Such non-GDNF family ligand pre-pro-region polypeptides and encoding polynucleotides are well known in the art.

Thus, chimeras of the GDNF family ligand can comprise an N-terminal region from any protein, pro-protein, or pre-pro-protein. This can be utilized, for example, to target the protein to a particular cellular region, or outside of the cell. Alternatively, GFRα-RET activating, truncated GDNF family members (including chimeras) containing only a portion of, or entirely lacking an N-terminal region can be made.

Although it is not intended that the inventors herein be bound by any theory, it is thought that the chimeric GDNF family ligands identified herein may exist as dimers in their biologically active form in a manner consistent with what is known for other factors of the TGF-β superfamily. The chimeras may be used in homodimers or heterodimers. It is believed that monomers of the chimeras will associate under physiological conditions into homodimers A preferred chimera according to the present invention is prepared in pure form by recombinant DNA technology. By "pure form" or "purified form" or "substantially purified form" it is meant that a chimera composition is substantially free of other proteins which are not the chimera. Preferably, a substantially purified chimera composition comprises at least about 50 percent chimera on a molar basis compared to total proteins or other macromolecular species present. More preferably, a substantially purified chimera composition will comprise at least about 80 to about 90 mole percent of the total protein or other macromolecular species present and still more preferably, at least about 95 mole percent or greater.

A recombinant chimera may be made by expressing a DNA sequence encoding the chimera in a suitable transformed host cell. Using methods well known in the art, the DNA encoding the chimera may be linked to an expression vector and transformed into a host cell, and conditions established that are suitable for expression of the chimera by the transformed cell.

Any suitable expression vector may be employed to produce a recombinant chimera such as, for example, the mammalian expression vector pCB6 (Brewer, *Meth Cell Biol* 43: 233–245, 1994) or the *E. coli* pET expression vectors, specifically, pET-30a (Studier et al., *Methods Enzymol* 185: 60–89, 1990). Other suitable expression vectors for expression in mammalian and bacterial cells are known in the art as are expression vectors for use in yeast or insect cells. Baculovirus expression systems can also be employed.

A number of cell types may be suitable as host cells for expression of a recombinant chimera. Mammalian host cells include, but are not limited to, monkey COS cells, Chinese Hamster Ovary (CHO) cells, human kidney 293 cells, human epidermal A431 cells, human Colo 205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK and Jurkat cells. Yeast strains that may act as suitable host cells include *Saccharomyces cerevisiae, Schizosaccharomyces pombe, Kluyveromyces* strains, *Candida*, and any other yeast strain capable of expressing heterologous proteins. Host bacterial strains include *Escherichia coli, Bacillus subtilis, Salmonella typhimurium* and any other bacterial strain capable of expressing heterologous proteins. If the polypeptide is made in yeast or bacteria, it may be necessary to modify the polypeptide, for example, by phosphorylation or glycosylation of the appropriate sites using known chemical or enzymatic methods, to obtain a biologically active polypeptide.

The chimeras of the present invention can also be expressed in transgenic plants (see, for example, U.S. Pat. No. 5,679,880) or transgenic animals such as, for example, cows, goats, pig, or sheep whose somatic or germ cells contain a nucleotide sequence encoding the chimera.

The expressed chimera can be purified using known purification procedures, such as gel filtration and ion exchange chromatography. Purification may also include affinity chromatography using an agent that will specifically bind the chimeric polypeptide, such as a polyclonal or monoclonal antibody raised against the mature chimera or fragment thereof. Other affinity resins typically used in protein purification may also be used such as concanavalin A-agarose, HEPARIN-TOYOPEARL® or CIBACROM BLUE 3GA SEPHAROSE®. Purification of the chimera can also include one or more steps involving hydrophobic interaction chromatography using such resins as phenyl ether, butyl ether, or propyl ether.

It is also contemplated that the chimera may be expressed as a fusion protein to facilitate purification. Such fusion proteins, for example, include the chimera amino acid sequence fused to a histidine tag, as well as the chimera amino acid sequence fused to the amino acid sequence of maltose binding protein (MBP), glutathione-S-transferase (GST) or thioredoxin (TRX). Similarly, the invention chimera can be tagged with a heterologous epitope, such as a FLAG® epitope, and subsequently purified by immunoaffinity chromatography using an antibody that specifically binds the epitope. Kits for expression and purification of such fusion proteins and tagged proteins are commercially available. A preferred fusion protein is one containing both a histidine tag and a FLAG® tag, e.g. as described in Example 1.

The recombinant chimeras may also be expressed as monomeric units or such monomeric form may be produced by preparation under reducing conditions. In such instances refolding and renaturation can be accomplished using one of the agents noted above that is known to promote dissociation/association of proteins. For example, the monomeric form can be incubated with dithiothreitol followed by incubation with oxidized glutathione disodium salt followed by incubation with a buffer containing a refolding agent such as urea.

The chimeras of the present invention may also be produced by chemical synthesis using methods known to those skilled in the art.

The present invention also encompasses isolated polynucleotides comprising nucleotide sequences that encode any of the chimeras described herein. As used herein, a polynucleotide includes DNA and/or RNA and thus the nucleotide sequences recited in the Sequence Listing as DNA sequences also include the identical RNA sequences with uracil substituted for thymine residues.

The present invention also encompasses vectors comprising an expression regulatory element operably linked to any of the chimera-encoding nucleotide sequences included within the scope of the invention. This invention also includes host cells, of any variety, that have been transformed with such vectors.

In yet another embodiment, a polynucleotide which specifically hybridizes to a chimera-encoding polynucleotide or to its complement is provided. Specific hybridization is defined herein as the formation of hybrids between a polynucleotide, including oligonucleotides, and a specific reference polynucleotide (e.g., a polynucleotide comprising a nucleotide sequence complementary to a nucleotide sequence encoding a chimera) wherein the polynucleotide preferentially hybridizes to the specific chimera over other GDNF family ligands. Specific hybridization is preferably done under high stringency conditions which, as well understood by those skilled in the art, can readily be determined by adjusting several factors during hybridization and during the washing procedure, including temperature, ionic strength, length of hybridization or washing times, and concentration of formamide (see for example, Sambrook, Fritsch and Maniatis., *Molecular Cloning: a Laboratory Manual, 2d Ed., Vols.* 1–3, Cold Spring Harbor Laboratory Press, Plainview N.Y. 11803, 1989)

The chimeras of the present invention would be expected to promote the survival and growth of neuronal as well as non-neuronal cells (see, e.g., Examples 2 and 4 herein). As discussed above, GDNF, neurturin, artemin and persephin influence a broad spectrum of neuronal populations in the peripheral and central nervous systems and the invention chimeras would be expected to also have such an effect. Moreover, all other growth factors isolated to date have been shown to act on many different cell types (for example see Scully and Otten, *Cell Biol Int* 19: 459–469, 1005; Hefti, *Neurotrophic Factor Therapy* 25: 1418–1435, 1994 which are incorporated by reference). As an example of the actions of neurotrophic factors on non-neuronal tissues, the prototypical neurotrophic factor, NGF, also acts upon mast cells to increase their number when injected into newborn rats (Aloe, *J Neuroimmunol* 18: 1–12, 1988). In addition, mast cells express the trk receptor and respond to NGF such that NGF is a mast cell secretogogue and survival promoting factor (Horigome et al., *J Biol Chem* 269: 2695–2707, 1994). Moreover, members of the TGF-β superfamily act on many cell types of different function and embryologic origin. For example, GDNF activation of GFRα1 is apparently critical in kidney organogenesis. Thus, it is likely that the invention chimeras will have trophic activity on a variety of different neuronal cells, both peripheral and central, as well as on non-neuronal cells.

The present invention also includes therapeutic or pharmaceutical compositions comprising a chimera of the present invention in an effective amount for providing trophic support to cells in patients with cellular degeneration or dysfunction and a method comprising administering a therapeutically effective amount of the chimera to a cell ex vivo or in vivo. The term "trophic support" is used herein to mean that a growth factor such as the invention chimeras provides sufficient nourishment to a cell such that the cell maintains or recovers at least one or more of its normal functions.

The compositions and methods of the present invention are useful for treating a number of degenerative diseases and anaplastic diseases. Where the cellular degeneration, dysfunction or anaplasia involves neurons, the diseases include, but are not limited to peripheral neuropathy, amyotrophic lateral sclerosis, Alzheimer's disease, Parkinson's disease, Huntington's disease, diabetes, AIDS, ischemic stroke, acute brain injury, acute spinal cord injury, nervous system tumors such as neuroblastomas, multiple sclerosis, peripheral nerve trauma or injury, exposure to neurotoxins, metabolic diseases such as diabetes or renal dysfunctions and damage caused by infectious agents or chemotherapy. In addition, compositions of the invention chimeras can be used to treat enteric diseases such as idiopathic constipation or constipation associated with Parkinson's disease, spinal cord injury or use of opiate pain-killers. If the cellular degeneration or dysfunction involves nonneuronal cells such as bone marrow cells, a chimera may be useful in treating diseases including, but not limited to disorders of insufficient blood cells such as, for example, leukopenias including eosinopenia and/or basopenia, lymphopenia, monocytopenia, neutropenia, anemias, thrombocytopenia as well as an insufficiency of stem cells for any of the above. The cellular degeneration or dysfunction can also involve myocardial muscle cells in diseases such as cardiomyopathy and congestive heart failure. In addition small cell lung carcinoma can be treated with polypeptide or polynucleotide compositions of the invention chimeras.

Treatment of enteric diseases with the chimeras includes the treatment of enteric neuropathies. The enteric nervous system is a complex collection of nerves that control the function of the gastrointestinal system, including gastrointestinal motility. Initial clinical studies with the NT-3, have shown that this neurotrophic factor increases gastrointestinal motility in normal volunteers and in patients suffering from peripheral neuropathies. Heuckeroth et al., *Dev Biol* 200: 116–29, 1998. Similarly, it is believed that the invention chimeras as well as the other GDNF family ligands will show activity on enteric neurons. As a result, it is believed that the chimeras will be useful in treating enteric neuropathies such as in patients suffering from severe idiopathic constipation as well as patients suffering from constipation associated with Parkinson's disease, spinal cord injury, use of opiate pain-killers, and the like.

Whether the invention chimeras would be effective in the treatment of a particular cell type or tissues can be readily determined by one skilled in the art using any of a variety of assays khown in the art. For example, with respect to providing trophic support for cells, trophic factors can produce beneficial biochemical and morphological effects and, under some circumstances, will promote cell survival. With respect to neurons, it is known in the art that depriving a neuron of trophic support results in a decrease in metabolic activity, i.e., glucose uptake, RNA synthesis and protein synthesis, required for normal function and growth. Deckwerth and Johnson, *J. Cell Biol.* 123: 1207–1222, 1993. Removal of trophic support also results in a reduction in size of the cell body of the neuron. Presumably as a consequence of the loss of the metabolic effects of trophic factors, trophic factor deprivation results in a decrease or cessation of process outgrowth and may result in retraction of neuronal processes. In addition to the requirement of trophic factor for these aspects of neuronal biology, the neuron may require the neurotrophic factor to maintain survival. Thus, survival assays are a frequently used means to detect or quantitate the actions of a neurotrophic factor. However, trophic support can also be manifest as morphological, biochemical, and/or functional changes independent of neuronal number or any effect on survival.

As discussed above, growth factors can produce a cell differentiation in addition to providing trophic support for cells. Thus, it is believed that the invention chimeras and polynucleotides encoding them can be beneficially used to produce a differentiation of anaplastic cells such as cancer cells. In particular, the chimeras can be used to treat nervous system tumors such as neuroblastomas. In addition, small cell lung carcinomas are known to express RET. Hence, it is believed that the chimeras can also be used to treat small cell lung carcinomas.

It is also contemplated that the eliciting of trophic support and/or differentiation can be achieved by administering a chimera along with a GFRα1 polypeptide (and/or GFRα2 or GFRα3, for the neurturin or artemin mimics, respectively) or by administering a polynucleotide encoding the chimera and the appropriate GFRα polynucleotide using the methods previously described with GDNF in Treanor et al., *Nature* 382: 80–83, 1996. Sequences for GFRα1 are known in the art. See, e.g., Genbank Accession numbers NP_005255 for a human polypeptide sequence and NM_005264 for a polynucleotide sequence encoding human GFRα1.

The invention chimeras are believed to bind to GFRα1 (and GFRα2 or GFRα3 in the case of the neurturin or artemin mimics, respectively) in the absence of RET and it is believed that the resulting ligand/coreceptor complex is capable of binding to and activating RET receptors expressed by a target cell. Thus, treatment with a chimera and the appropriate GFPα would be expected to increase the sensitivity of cells normally responsive to the chimera and would also be expected to provide trophic support to cells that express RET but that are not normally responsive to the chimera. Preferably, the chimera and GFRα polypeptides are from the same species, i.e., human. It is also preferred that the GFRα polypeptide be in soluble form, i.e., that it lack the GPI linkage to avoid potential undesirable interactions with cell membranes. As used herein a GFRα polypeptide is intended to include the mature protein with or without the GPI anchor, as well as GFRα fragments, particularly soluble fragments lacking a GPI anchor, that are capable of binding to both the invention chimeras and RET with such binding leading to the activation of RET.

The therapeutic or pharmaceutical compositions of the present invention can be administered by any suitable route known in the art including for example intravenous, subcutaneous, intramuscular, transdermal, intrathecal or intracerebral. Administration can be either rapid as by injection or over a period of time as by slow infusion or administration of a slow release formulation. For treating tissues in the central nervous system, administration can be by injection or infusion into the cerebrospinal fluid (CSF). When it is intended that an invention chimera be administered to cells in the central nervous system, administration can be with one or more agents capable of promoting penetration of the chimera across the blood-brain barrier.

The invention chimeras can also be linked or conjugated with agents that provide desirable pharmaceutical or pharmacodynamic properties. For example, a chimera can be coupled to any substance known in the art to promote penetration or transport across the blood-brain barrier such as an antibody to the transferrin receptor, and administered by intravenous injection (See for example, Friden et al., *Science* 259:373–377, 1993). Furthermore, a chimera can be stably linked to a polymer such as polyethylene glycol to obtain desirable properties of solubility, stability, half-life and other pharmaceutically advantageous properties. (See for example Davis et al. *Enzyme Eng* 4: 169–73, 1978; Burnham, *Am J Hosp Pharm* 51: 210–218, 1994).

Preferably, a chimera of the present invention is administered with a carrier such as liposomes or polymers containing a targeting moiety to limit delivery of the chimera to targeted cells. Examples of targeting moieties include but are not limited to antibodies, ligands or receptors to specific cell surface molecules.

For nonparenteral administration, the compositions can also include absorption enhancers which increase the pore size of the mucosal membrane. Such absorption enhancers include sodium deoxycholate, sodium glycocholate, dimethyl-β-cyclodextrin, lauroyl-1-lysophosphatidylcholine and other substances having structural similarities to the phospholipid domains of the mucosal membrane.

The compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. The invention chimeras can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion into the cerebrospinal fluid by continuous or periodic infusion.

Dose administration can be repeated depending upon the pharmacokinetic parameters of the dosage formulation and the route of administration used.

It is also contemplated that certain formulations containing a chimera are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and promote absorption such as, for example, surface active agents.

The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art based on the activity of the chimera for a particular cell type in vitro. The activity of invention chimeras on various peripheral and central neurons in culture is described below and its activity on a particular target cell type can be determined by routine experimentation. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

In one embodiment of this invention, an invention chimera may be therapeutically administered by implanting into patients vectors or cells capable of producing a biologically-active form of the chimera or a precursor of the chimera, i.e. a molecule that can be readily converted to a biological-active form of the chimera by the body. In one approach cells that secrete the chimera may be encapsulated into semipermeable membranes for implantation into a patient. In some embodiments, the cells are transformed to express and secrete both the chimera and the appropriate GFRα, preferably in a soluble form. It is preferred that the cell be of human origin and that the chimera be derived from human GDNF family ligands when the patient is human. However, the formulations and methods herein can be used for veterinary as well as human applications and the term "patient" as used herein is intended to include human and veterinary patients.

Cells can be grown ex vivo for use in transplantation or engraftment into patients (Muench et al., *Leuk & Lymph* 16: 1–11, 1994). In another embodiment of the present invention, an invention chimera can be used to promote the ex vivo survival or expansion of cells for transplantation or engraftment. Current methods have used bioreactor culture systems containing factors such as erythropoietin, colony stimulating factors, stem cell factor, and interleukins to expand hematopoietic progenitor cells for erythrocytes, monocytes, neutrophils, and lymphocytes (Verfaillie, *Stem Cells* 12: 466–476, 1994). These stem cells can be isolated from the marrow of human donors, from human peripheral blood, or from umbilical cord blood cells. The expanded blood cells are used to treat patients who lack these cells as a result of specific disease conditions or as a result of high dose chemotherapy for treatment of malignancy (George, *Stem Cells* 12(*Suppl* 1): 249–255, 1994). In the case of cell transplant after chemotherapy, autologous transplants can be performed by removing bone marrow cells before chemotherapy, expanding the cells ex vivo using methods that also function to purge malignant cells, and transplanting the expanded cells back into the patient following chemotherapy (for review see Rummel and Van Zant, *J Hematotherapy* 3: 213–218, 1994).

It is also believed that an invention chimera with or without the appropriate GFRα can be used for the ex vivo expansion of precursor cells in the nervous system. Transplant or engraftment of cells is currently being explored as a therapy for diseases in which certain populations of neurons are lost due to degeneration such as, for example, in Parkinson's disease (Bjorklund, *Curr Opin Neurobiol* 2: 683–689, 1992) and spinal cord injury. Neuronal precursor cells can be obtained from animal or human donors or from human fetal tissue and then expanded in culture using a chimera of the present invention. These cells can then be engrafted into patients where they would function to replace some of the cells lost due to degeneration. Because neurotrophins have been shown to be capable of stimulating the survival and proliferation of neuronal precursor cells such as, for example, NT-3 stimulation of sympathetic neuroblast cells (Birren et al., *Develop* 119: 597–610, 1993), the chimera could also function in similar ways during the development of the nervous system and could be useful in the ex vivo expansion of neuronal cells.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

The procedures disclosed herein which involve the molecular manipulation of nucleic acids are known to those skilled in the art. See generally Fredrick M. Ausubel et al. (1995), "Short Protocols in Molecular Biology", John Wiley and Sons, and Joseph Sambrook et al. (1989), "Molecular Cloning, A Laboratory Manual", second ed., Cold Spring Harbor Laboratory Press, which are both incorporated by reference.

EXAMPLE 1

This example illustrates that the N-terminal extension of GDNF is not required for activity.

An alignment of the mature rat GDNF with mouse neurturin, artemin and persephin is shown in FIG. 1. This amino acid sequence comparison and alignment was performed using the MegAlign program of the DNAstar software package. Rat GDNF was the basis for all mutagenesis in this example because its structure has been determined (Eigenbrot and Gerber, *Nat. Struct. Biol.* 4: 435–438, 1997). For this and all other examples, the amino acid sequence of rat GDNF (SEQ ID NO:12) and mouse neurturin (SEQ ID NO:14) and persephin (SEQ ID NO:2), and human artemin (SEQ ID NO:15) were used for all constructs. The largest notable difference between the GDNF family ligands is the N-terminal extension before the first structural cysteine, which varies from 40 amino acids in GDNF (SEQ ID ID NO:18) to only 5 amino acids in neurturin (SEQ ID NO:18) and persephin (amino acids 1–5 of SEQ ID NOs 1–3), and shows little similarity between the different family members. Furthermore GDNF, neurturin and artemin have multiple RXXR consensus subtilisin-like proprotein convertase (SPC) cleavage sites (Molloy et al., *J. Biol. Chem.* 267: 16396–16402, 1992), and therefore multiple isoforms of these extensions are possible. The ones shown are consistent with N-terminal sequencing of GDNF and neurturin (Kotzbauer et al., *Nature* 384: 467–470, 1996), the single cleavage site in PSPN (Milbrandt et al., supra), and a cleavage site conserved between mouse and human artemin (Baloh et al., supra).

Figure 2A:
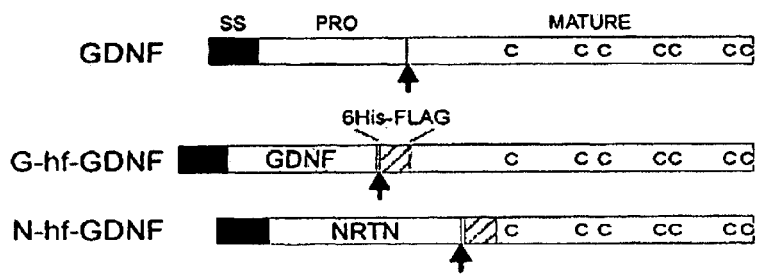
FIG. 2A depicts a schematic diagram of wild-type and tagged GDNF constructs, where the site of proprotein convertase cleavage of GDNF is indicated by the arrow (SS—signal sequence, PRO—pro domain, MATURE—mature processed monomer), where GDNF with a 6-histidine and FLAG® tag inserted two residues after the RXXR cleavage site is designated "G-hf-GDNF" and where GDNF with the histidine and FLAG® tag wherein the GDNF pro sequence is substituted with the neurturin pro sequence is designated "N-hf-GDNF"

To determine if the large N-terminal extension of GDNF is required for its activity, the differential processing of GDNF and neurturin by mammalian cells was utilized. Chimeric constructs with the pre-pro region from neurturin attached to GDNF were generated, and both their processing and their ability to activate the GFRα1-RET receptor complex was assessed (FIG. 2). Tandem 6×Histidine and FLAG® tags were inserted after the RXXR cleavage site of GDNF or neurturin to allow purification and tracking of the proteins (FIG. 2A). For mutant G-hf-GDNF the 6His-FLAG® tag was inserted between the third and fourth residue of mature GDNF, making the sequence N-... RLKR˽SPD-YKDDDDK-QAAALPRRERNRQAAAASP-ENSRGKGRRGQRGKNRGCVLTAIHLNVTD-LGLGYETKEELIFRYCSGSCEAAETMYDKILKNLSR-SRRLTSDKVGQACCRPVAFDDDLSFLDDSLVYHIL-RKHSAKRCGCI (SEQ ID NO:29). For mutant P-hf-PSPN, the tag was inserted between the third and fourth residue of mature PSPN, resulting in N-... RLPR˽ALA-HHHHHHDYKDDDDKGSCRLWSLTLPVAE-LGLGYASEEKVIFRYCAGSCPOEARTQHSLVLARLRG-RGRAHGRPCCQPTSYADVTFLDDQHHWQQLPQ-LSAAACGCGG (SEQ ID NO: 30). All mutants were produced by fusion PCR mutagenesis. PCR products were directly cloned into the MluI and XbaI sites of plasmid pCB6 (Brewer, *Meth Cell Biol.* 43: 233–245, 1994) and the inserts sequenced entirely. For mutant N-hf-GDNF, residues 1–38 were truncated from mature GDNF, and attached to the pre-pro region of NRTN. The resulting sequence was N-... RRAR˽PGA-HHHHHHDYKDDDDK-RGCVLTA-IHLNVTDLGLGYETKEELIFRYCSGSCEAAETMYD-KILKNLSRSRRLTSDKVGQACCRPVAFDDD-LSFLDDSLVYHILRKHSAKRCGCI (SEQ ID NO: 31)

Figure 2B:
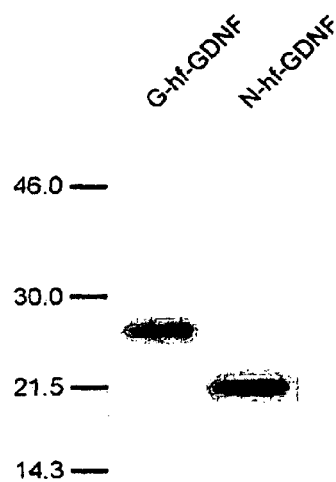
FIG. 2B is an image of a FLAG® inmmunoblot demonstrating the production of tagged GDNF proteins in COS cells, where the immunoblot indicates that N-hf-GDNF produces GDNF with the 40 amino acid N-terminal extension replaced by two amino acids and the tandem His-FLAG tags.

The mutant proteins were produced in COS cells as follows. For mutant protein production in COS cells, expression plasmids were transfected using the DEAE-dextran/Chloroquine method (Seed and Aruffo, *Proc. Natl. Acad. Sci. U.S.A.* 84: 3365–3369, 1987). COS cells were plated onto 10 cm or 15 cm dishes, transfected, and switched to Delbecco's Modified Eagle's Media containing 1% fetal calf serum. After 4–5 days, conditioned medium was collected, cleared, and either concentrated using Centriprep-10 concentrators (Amicon) or purified by nickel chromatography (Qiagen). Proteins were visualized by immunoblotting with anti-FLAG® M2 monoclonal antibody (Sigma). Relative quantities of FLAG®-tagged proteins were determined by an ELISA also using the anti-FLAG® M2 antibody. The absolute concentration of GDNF in purified and conditioned medium samples was determined for the G-hf-GDNF construct using the GDNF E-$_{MAX}$ ELISA kit following the manufacturer's instructions (Promega). As shown in FIG. 2B, monomeric G-hf-GDNF ran at ~25 kD, and N-hf-GDNF at ~21.5 kD, consistent with processing at the predicted RXXR cleavage sites from GDNF and neurturin. Therefore N-hf-GDNF produces GDNF with the 40 amino acid N-terminal extension replaced by two amino acids and the tandem His-FLAG® tags. When expressed in COS cells, similar quantities of tagged GDNF with its own pro-region (G-hf-GDNF) or the neurturin pro-region (N-hf-GDNF) could be purified from conditioned medium using nickel chromatography (FIG. 2B). Only species corresponding to the expected processing events were observed, indicating that the pro-domains of neurturin and GDNF are sufficient to direct proper processing of their different N-terminal extensions.

Figure 2C:
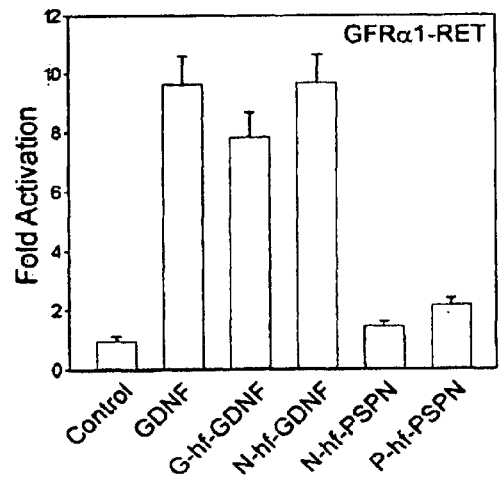
FIG. 2C is a graph showing the ability of tagged full-length and truncated GDNF to activate the GFRα1-RET receptor and the inability of tagged persephin in with its own (P-hf-PSPN) or neurturin's pro region (N-hf-PSPN) to activate GFRα1-RET.

To assess the ability of these proteins to activate the high-affinity GDNF receptor, GFRα1-RET, the Gal4-Elk1/Gal4-luciferase reporter system was used as described previously (Baloh et al., supra). This system monitors the level of RET activation of the MAP kinase pathway, which induces the Gal4-Elk1 fusion protein to activate the Gal4-luciferase reporter, giving a facile measure of receptor activation (Worby et al., *J Biol Chem* 273: 3502–3508, 1998; York et al., *Nature* 392: 622–626, 1988). RET-3T3 cells were plated at 85,000 cells/well in 12-well plates, and transfected using Superfect (Qiagen) with the reporter plasmids (250 ng/well Gal4-Luc, 50 ng/well Gal4-Elk), CMV-lacZ (50 ng/well) for transfection normalization, CMV-GFRα1 (250 ng/well) expression plasmid, the mutant GFL construct (250 ng/well) and 650 ng/well pBluescript as carrier for a total of 1.5 µg DNA/well. Cells were switched to 0.5% serum-containing medium the morning after transfection and harvested 36 hours later. The average luciferase activity of duplicate or triplicate samples were normalized to β-galactosidase activity of the cotransfected lacZ reporter. As shown in FIG. 2C, wild-type GDNF, G-hf-GDNF and N-hf-GDNF all showed comparable activation of GFRα1-RET in this assay, whereas tagged PSPN constructs with either the PSPN or neurturin pro-region did not activate the receptor. These results are consistent with previous receptor activation and binding experiments indicating that GDNF, but not PSPN, can bind and activate RET through GFRα1 (Baloh et al., supra; Milbrandt et al., supra). Furthermore, these data indicate that the N-terminal extension of GDNF is not required for its ability to activate the GFRα1-RET receptor complex, and the location of the epitope tag does not interfere with the function of GDNF.

The N-terminal extension before the first structural cystine-knot cysteine is highly variable amongst the TGF-β superfamily members. In the case of TGF-β2, it exists as a short α-helix and is stabilized by an additional disulfide bond relative to other members of the superfamily (Daopin et al., supra; Schlunegger and Grutter, *Nature* 358: 430434, 1992). However, in GDNF and OP-1, the only other members of the TGP-β superfamily that have been crystallized, the 35–37 residue N-terminal extension was unresolved and therefore does not adopt a consistent conformation in solution (Eigenbrot and Gerber, supra; Griffith et al., *Proc. Natl. Acad. Sci. U.S.A.* 93: 878–883, 1996). Truncating the N-terminal extension did not affect GDNF's ability to activate its receptors. This is consistent with experiments characterizing monoclonal antibodies against GDNF that also suggested the N-terminal extension is not required for receptor binding or bioactivity (Xu et al., *J. Neurochem.* 70: 1383–1393, 1998).

EXAMPLE 2

This example illustrates the use of homologue scanning to identify critical GDNF regions for activation of GFRα1-RET and GFRα2-RET.

Figure 3A:
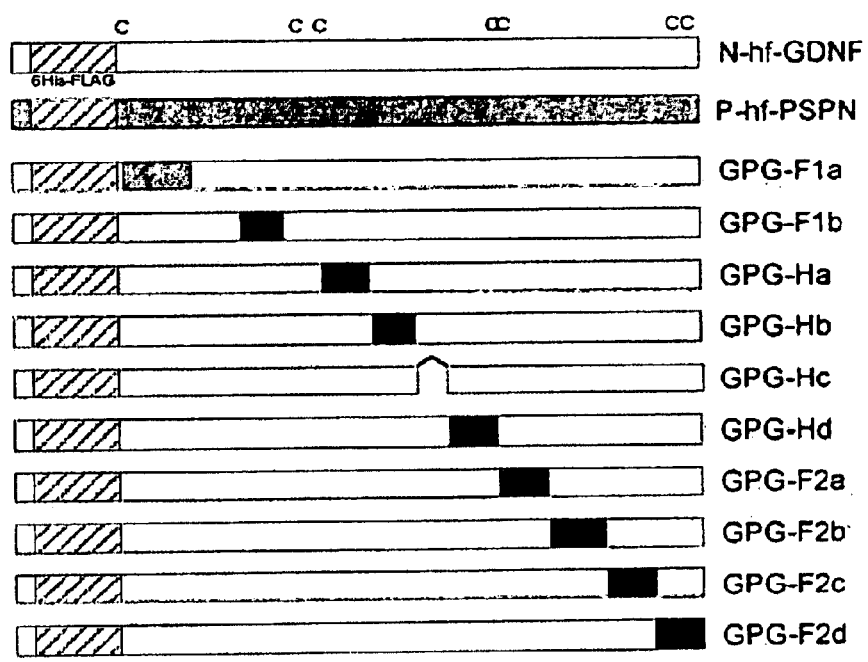
FIG. 3A is a schematic representation of the mature region from GDNF, persephin and the homologue-scanning mutants, where GPG signifies a chimera comprising primarily GDNF (open portions of figures) but having the portion of GDNF indicated by shading replaced by a homologous portion of persephin; further where mutant GPC-Hc is a deletion of amino acids 88–92 of mature GDNF to correspond with the lack of these residues in PSPN, and where the sequence of the replacements in these mutants are shown in FIG. 1.
Figure 3B:
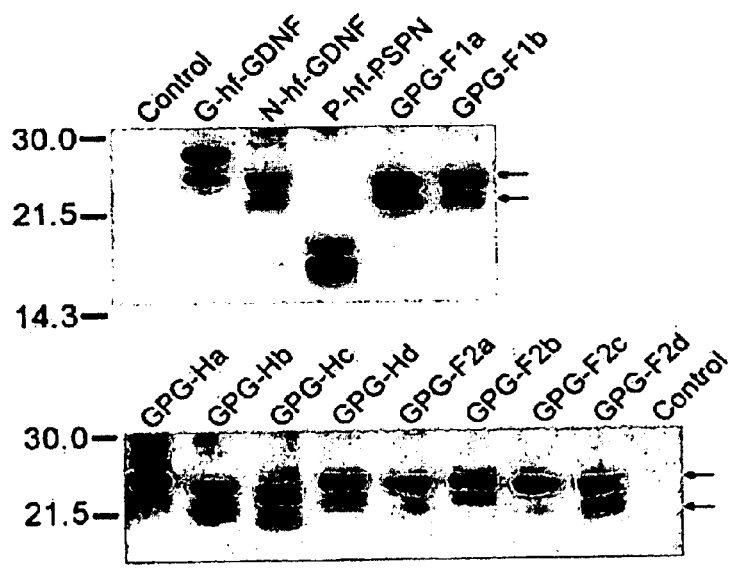
FIG. 3B is a photograph of an anti-FLAG® immunoblot of homologue scanning mutants from transfected COS cell lysates, where the two major bands indicated by arrows represent the unprocessed (top) and mature (bottom) forms of the mutants, since the lower band corresponds in size to the secreted product as shown in FIG. 2B.
Figure 6A:
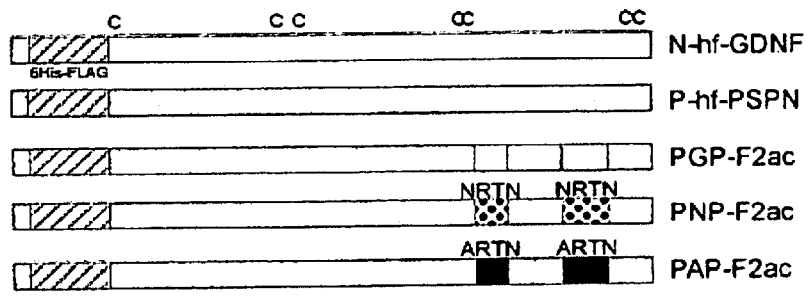
FIG. 6A is a schematic diagram depicting the structures of N-hf-GDNF, P-hf-PSPN, PGP-F2ac, PNP-F2ac, and PAP-F2ac.
Figure 6B:
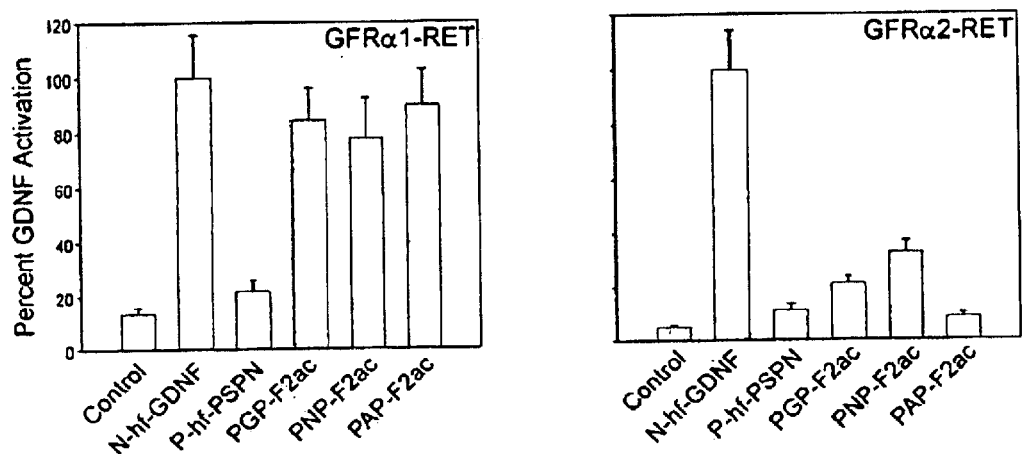
FIG. 6B is two graphs showing the ability or inability of the five molecules depicted in FIG. 6A to activate GFRα1-RET (left side) and GFRα2-RET (right side)
Figure 5E:
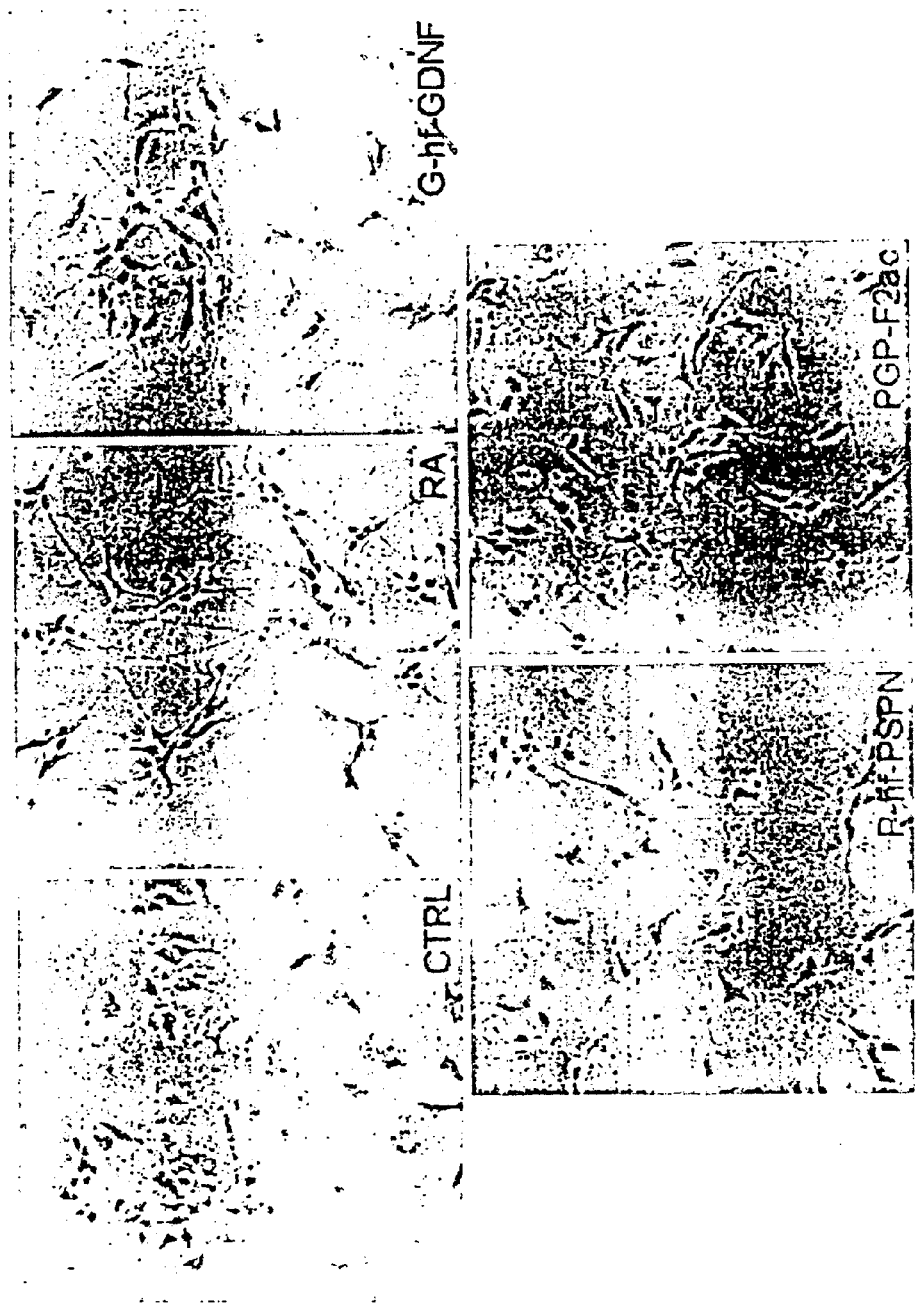
FIG. 5E are photographs of SH-SY5Y neuroblastoma cells cultured in the presence of no factor (CTRL), retinoic acid (RA; 10 μM) or conditioned medium from COS cells expressing the indicated construct, showing that GDNF and PGP-F2ac stimulates neurite outgrowth in these cells, whereas persephin does not.

Although the crystal structure of GDNF is known, the molecular determinants for GDNF-GFRα receptor binding and specificity are currently undefined. To identify regions of GDNF that are required for its ability to activate the GFRα1-RET receptor complex, homologue-scanning mutagenesis was utilized together with the receptor activation assay described in Example 1. Ten GDNF mutants (termed "GPG" mutants) were generated by replacing blocks of non-conserved sequence from PSPN into GDNF (FIG. 3; see FIG. 1 for sequence changes). This method allows comprehensive mutagenesis of sites responsible for the difference in the ability of GDNF and PSPN to activate GFRα1-RET, and is highly likely to maintain structural integrity of the mutants because the replacements are from a homologous (and likely structurally similar) protein. Expression plasmids for these mutants were produced as described in Example 1 using fusion PCR, and all were based on the N-hf-GDNF construct All mutants were produced at similar quantities when transfected into COS. cells, and processing of each appeared normal (FIG. 3B).

Comparison of the GPG mutants with GDNF revealed that although many mutants showed slightly decreased activity, only one (GPG-F2a) completely lost the ability to activate the GFRα1-RET receptor (FIG. 4A). This region was identified in a molecular model of GDNF. Molecular modeling and analysis was done using the SwissPDB viewer (Guex and Peitsch, *Electrophoresis* 18: 2714–2723, 1997), and models were rendered using Mole software (Applied Thermodynamics). The GDNF structure was modeled after entry 1AGQ (Eigenbrot and Gerber, supra) of the Protein Data Bank. The 'C/D' dimer from 1AGQ is shown, with the missing segment of monomer 'C' built as determined for monomer 'D'. The F2a region maps to the bottom of the GDNF molecule along the second finger (FIG. 4B; Eigenbrot and Gerber, supra). The only other notable mutant that consistently showed activity 60% or lower than full-length GDNF was GPG-F2c, which maps to the strand adjacent to region F2a along the bottom of the molecule.

It is well established that GDNF is also capable of activating the GFRα2-RET receptor, albeit with a lower affinity than neurturin (Baloh et al., *Neuron* 18: 793–802, 1997 Sanicola et al., *Proc. Natl. Acad. Sci., USA* 94: 6238–6243, 1997; Suvanto et al., *Hum. Molec. Genet.* 6: 1267–1273, 1997), whereas persephin cannot (Baloh et al., 1998, supra; Milbrandt et al., 1998, supra). Therefore, to compare the molecular determinants of GDNF required for GFRα1 vs. GFRα2 interaction, we tested the ability of this same panel of mutants to activate the GFRα2-RET receptor complex Several of the GPG mutants were significantly more attenuated in their ability to activate RET through GFRα2 than they were through GFRα1 (FIG. 4C). As before, mutant GPG-F2a was unable to activate the receptor. Interestingly, mutant GPG-F2c, which was the second most affected mutant in activating GFRα1-RET, showed essentially no activation of GFRα2-RET. Finally, the mutant that showed the most contrast in its ability to activate GFRα1-RET vs. GFRα2-RET was mutant GPG-Ha, which was severely affected only in its ability to activate GFRα2-RET. Interestingly, mapping these three regions to the GDNF crystal structure reveals that they form a continuous surface, with residues from F2a and F2c from one monomer directly adjacent to region Ha from the heel of the other monomer, suggesting a possible receptor-ligand interaction surface (FIG. 4D).

To summarize, the above mutagenesis data suggest that two adjacent regions of GDNF located along the second finger are necessary for interaction with both GFRα1 and GFRα2 (regions F2a and F2c), and that additional regions appear required for GDNF interaction with GFRα2.

EXAMPLE 3

This example illustrates that regions F2a and F2c from GDNF, neurturin, or artemin are sufficient for activating GFRα1-RET.

The homologue-scanning screen disclosed in Example 2 suggests several regions that are necessary for the full ability of GDNF to activate the GFRα1-RET receptor. However, using only loss of function analysis it is difficult to assess whether critical receptor-contact residues are being altered directly, or if the mutations induce structural changes that alter receptor contact surfaces elsewhere on the molecule. To identify if any of the critical regions identified above (either alone or in combination) are sufficient to allow binding and activation of the GFRα1-RET receptor complex, persephin mutants were generated with the putative critical regions from GDNF replacing the corresponding regions of persephin. It was then determined if these "PGP" mutants had gained the ability to activate the GFRα1-RET receptor complex (FIG. 5).

Two candidate regions, F2a and F2c, were initially evaluated along the second finger of GDNF, because mutant GPG-F2a was entirely inactive, and mutant GPG-F2c was the only other mutant that consistently showed decreased activation of GFRα1-RET. Replacement of either region F2a or F2c alone from GDNF into persephin was not sufficient to allow the resulting mutants (PGP-F2a or PGP-F2c) to activate GFRα1-RET. However, when both regions were placed into persephin the resulting mutant PGP-F2ac gained the ability to activate the GFRα1-RET receptor at a level comparable to full-length GDNF (FIG. 5B).

GFRα1-transfected Neuro2a cells (which endogenously express RET) were then treated with either GDNF or mutant PGP-F2ac as follows. Neuro2a cells were transiently transfected using Superfect with an expression plasm id for rat GFRα1 with a FLAG® tag inserted by PCR mutagenesis at after the signal sequence. Cells were treated with 25 ng/mL of the indicated factor for 6 hours, the cells were washed once with cold PBS, lysed, and immunoprecipitated using an anti-FLAG® M2 monoclonal antibody conjugated to agarose (Sigma). After washing, the immunoprecipitated samples were visualized by immunoblotting with an anti-RET antibody (C-9; Santa Cruz). Both GDNF and PGP-F2ac induced comparable receptor complex formation, demonstrating that PGP-F2ac had gained the ability to bind and induce GFRctI-RET complex formation (FIG. 5C).

To determine if mutant PGP-F2ac was also able to elicit biological responses comparable to GDNF, its ability to induce proliferation in the NBL-S neuroblastoma cell line was determined. This cell line expresses GFRα1 and RET and responds to GFRα1-RET agonists (GDNF, neurturin, artemin) by proliferation. The NBL-S proliferation assay was performed as described in Baloh et al., 1998, supra. Mutant PGP-F2ac purified from transiently transfected COS cell conditioned medium induced robust proliferation of NBL-S cells, similar to GDNF at all doses, whereas persephin did not (FIG. 5D). Furthermore, PGP-F2ac was also able to induce neurite outgrowth in the GFRα1-RET expressing neuroblastoma line SH-SY5Y (as evaluated according to the method of Baloh et al., 1998, supra) similar to GDNF (FIG. 5E).

Neurturin and artemin are also able to activate GFRα1-RET (Baloh et al., 1998, supra; Creedon et al., *Proc. Natl. Acad. Sci. US* 9 4: 7018–7023, 1997), and there was determined if the same regions (F2a and F2c) from these two additional GFRα1 agonists are also sufficient to activate the GFRα1-RET receptor (FIG. 6). Interestingly, the corresponding persephin mutants with regions F2a and F2c from neurturin and artemin were also capable of activating the GFRα1-RET receptor complex, at levels comparable to GDNF and PGP-F2ac (FIG. 6B). This indicates that elements of regions F2a and F2c from all the known GFRα1 agonists are sufficient to activate GFRα1-RET when placed in the context of persephin. Furthermore, these regions appear to be sufficient only for GFRα1-RET activation, as the same mutants did not activate GFRα2-RET comparably to GDNF (FIG. 6C). Mutants PNP-F2ac and PGP-F2ac did elicit low-level activation (less than 30% of GDNF) of GFRα2-RET, whereas PAP-F2ac did not. This is consistent with the ability of GDNF and neurturin, but not artemin to activate GFRα2-RET, and indicates that regions F2a and F2c are also involved in binding and activating GFRα2-RET, but that additional regions are required for full activation.

The mutagenesis reported here indicates that critical residues for GFRα receptor interaction and specificity are located in the second finger region of the GDNF molecule. However, while the use of homologue-scanning mutagenesis is ideally suited for identifying sites involved in differential receptor specificity, it cannot delineate all residues involved in receptor binding, as some of these are identical in GDNF and persephin. The fact that residues from region F2a and F2c are sufficient when placed in the context of persephin to activate GFRα1-RET indicates that residues in these regions are likely to be directly involved in binding to GFRα's. Although it is possible that the GDNF family ligands also contact RET in the active receptor complex, the fact that all members of the GDNF family ligands, including persephin, appear to signal through RET makes it doubtful that the regions identified by this mutagenesis scheme are involved in RET-interaction directly. However, because this analysis focused on functional activation of the GFRα-RET receptor complex rather than receptor binding assays the possibility cannot be excluded that some of the non-functional mutants produced here may still be capable of binding to the GFRα coreceptors, and potentially even function as receptor antagonists.

Figures 4A, 4C:
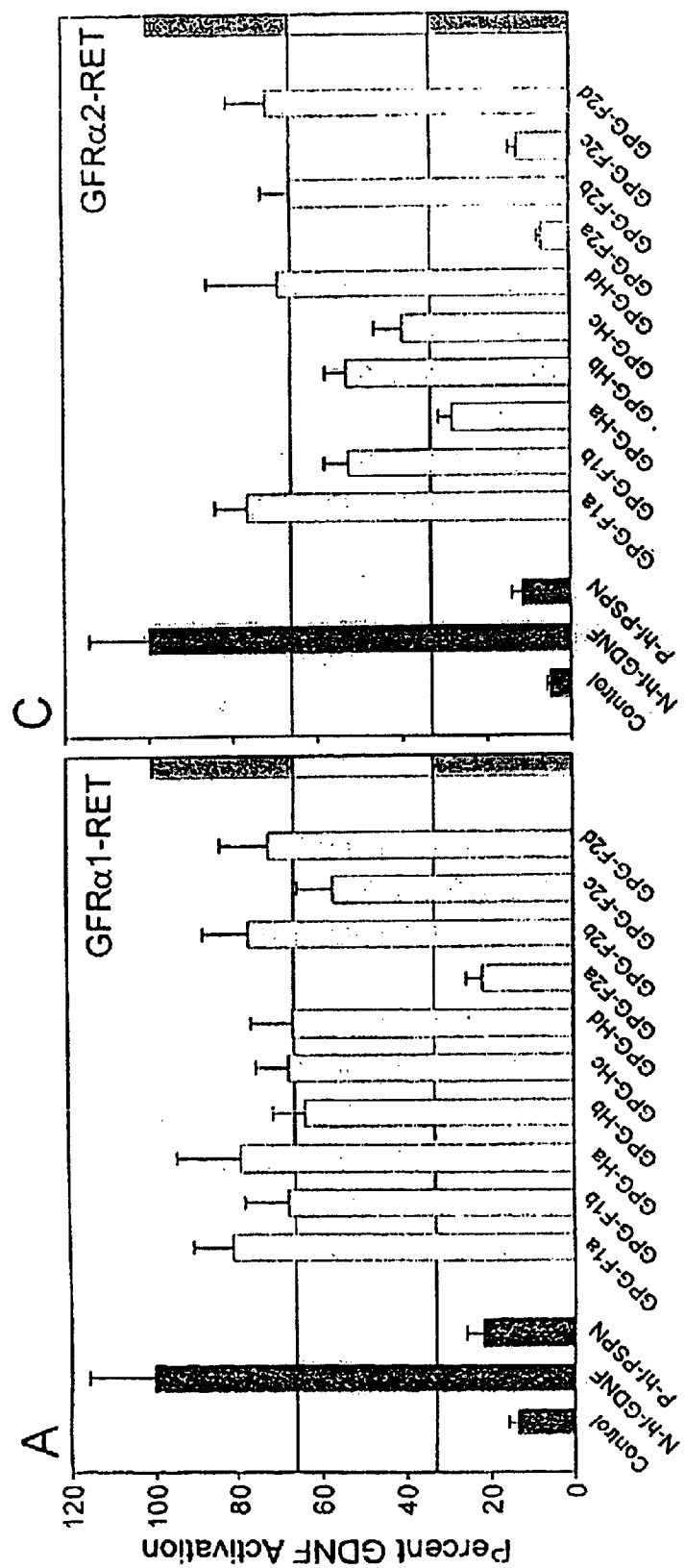
FIG. 4A is a graph showing relative GFRα1-RET receptor activation by homologue-scanning GDNF mutants, where values are represented as a percentage of reporter activation by GDNF and the mean and standard deviation of triplicate measurements from a representative experiment are shown, along with arbitrary boundary lines at 33% and 66% of wild-type GDNF activation.
FIG. 4C is a graph showing relative GFRα2-RET receptor activation by homologue-scanning GDNF mutants, where values are represented as a percentage of reporter activation by GDNF and the mean and standard deviation of duplicate measurements from a representative experiment are shown, along with arbitrary boundary lines at 33% and 66% of wild-type GDNF activation.

Current evidence suggests that the stoichiometry of the active receptor complex for GDNF is $(GDNF)_1 (GFR\alpha)_2 (RET)_2$ (Jing et al., Cell 85: 1113–1124, 1996). Residues from regions F2a and F2c project essentially from the bottom the GDNF structure, and form symmetric sites on both monomers of the molecule (see FIG. 4B). Interestingly, residues from region Ha (which is critical for GDNF-GFRα2, and ARTN-GFRα3 interaction) lie directly adjacent to regions F2a and F2c from the finger 2 region of the opposing monomer, and form continuous surfaces along the side and bottom of the molecule (see FIG. 4C). Because these regions are all critical for GFRα specificity, it appears that the molecular surface formed by the heel of one monomer and the second finger of the adjacent monomer form GFRα binding surfaces on GDNF.

Comparison of structure/function studies from other TGF-β and cystine-knot superfamily members reveals common themes in the location of receptor binding surfaces. The best characterized of these is the binding of vascular endothelial growth factor (VEGF) with its receptors KDR and Flt-1, where extensive mutagenesis and co-crystallization have been performed (Muller et al., Proc. Natl. Acad. Sci. U.S.A. 94: 7192–7197, 1997; Wiesmann et al., Cell 91: 695–704, 1997). Mutagenesis of VEGF identified a cluster of residues critical for KDR binding, several of which were along the adjacent β-strands of the second finger, similar to regions F2a and F2c identified here for GDNF. Furthermore, even though the orientation of the monomers in the VEGF dimer is different from GDNF, the receptor binding site on VEGF involves residues from finger 2 and the analogous heel region of the opposing monomer. Finally, mutagenesis of TGF-β indicates that the binding affinity of the different TGF-β isoforms for the TGF-β type II receptor is also determined by residues along the second finger of the molecule, analogous in location to region F2c (Burmester et al., Growth Factors 15: 231–242, 1998; Qian et al., J. Biol. Chem. 271: 30656–30662, 1996). Therefore it is possible that although the receptor systems and dimerization modes are strikingly different for these different cystine-knot superfamily proteins, the location of their receptor interaction surfaces may be quite similar.

EXAMPLE 4

This example illustrates that additional determinants are critical for neurturin to activate GFRα2-RET and artemin to activate GFRα3-RET.

Figure 4D:
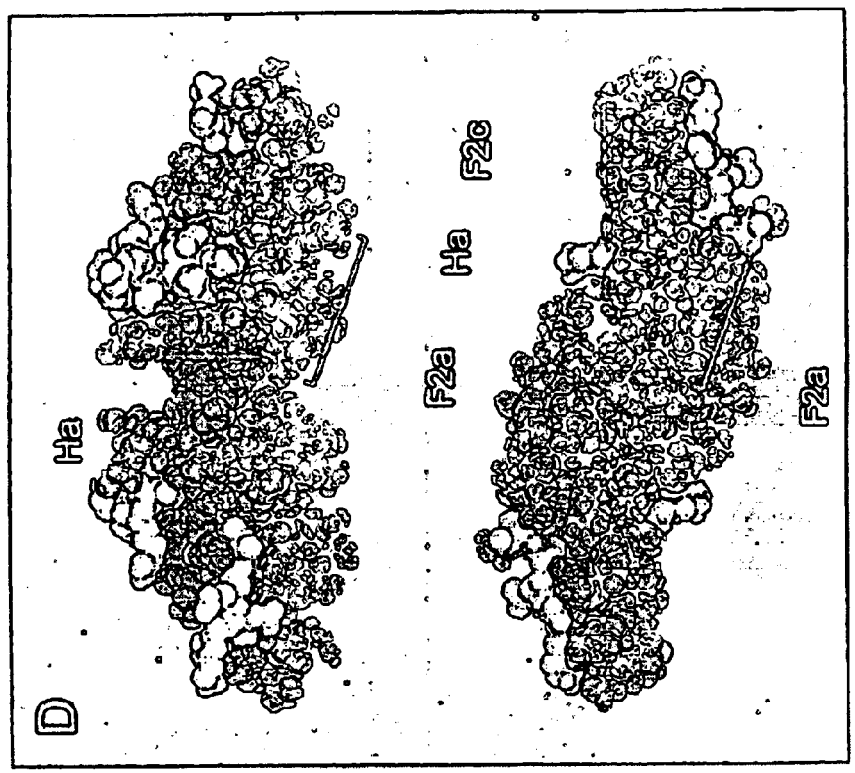
FIG. 4D depicts a space-filling model of the GDNF crystal structure, where the upper representation is a side-view of the GDNF dimer, and the lower representation is from a viewpoint below the dimer, showing putative critical GFRα2-RET interaction domains Ha, F2a, and F2c.
Figure 4B:
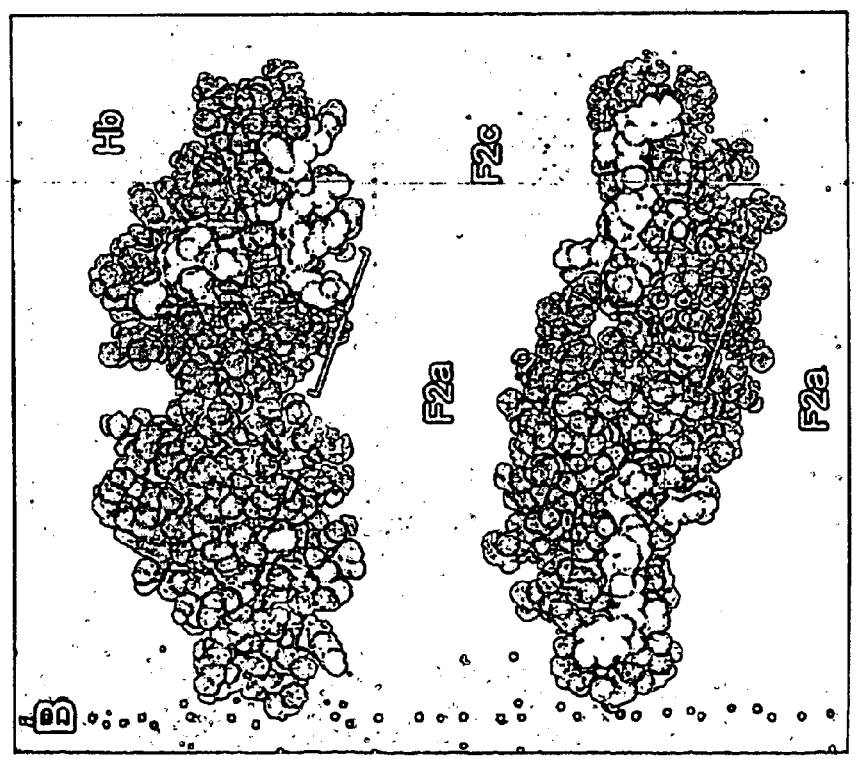
FIG. 4B depicts a space-filling model of the GDNF crystal structure, where the upper representation is a side-view of the GDNF dimer, and the lower representation is from a viewpoint below the dimer, showing putative critical GFRα1-RET interaction domains Hb, F2a, and F2c.
Figure 5B:
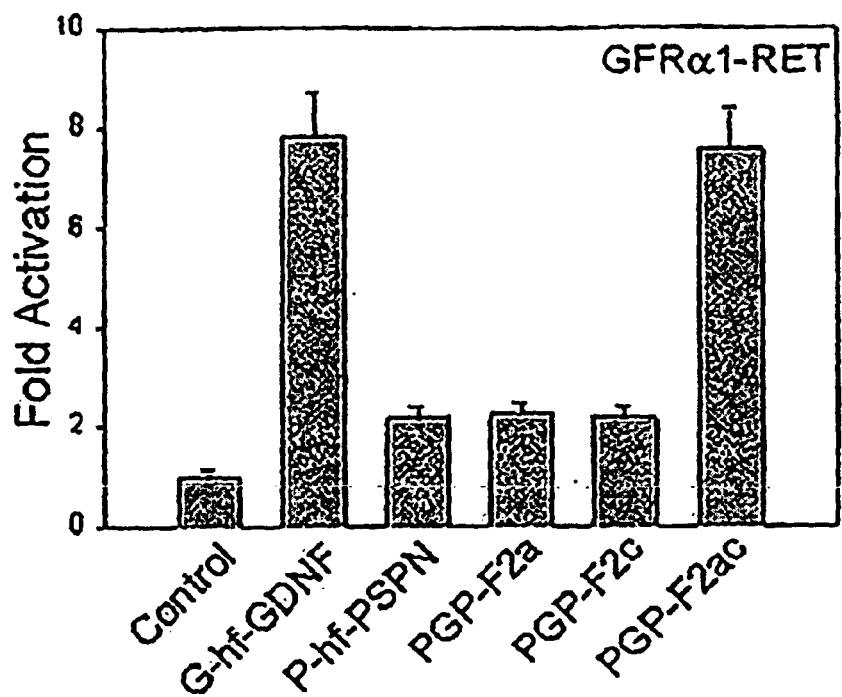
FIG. 5B is a graph showing the ability of PGP-F2ac to activate the GFRα1-RET receptor and the inability of other PGP chimeras and P-hf-PSPN to activate GFRα1-RET.
Figure 5D:
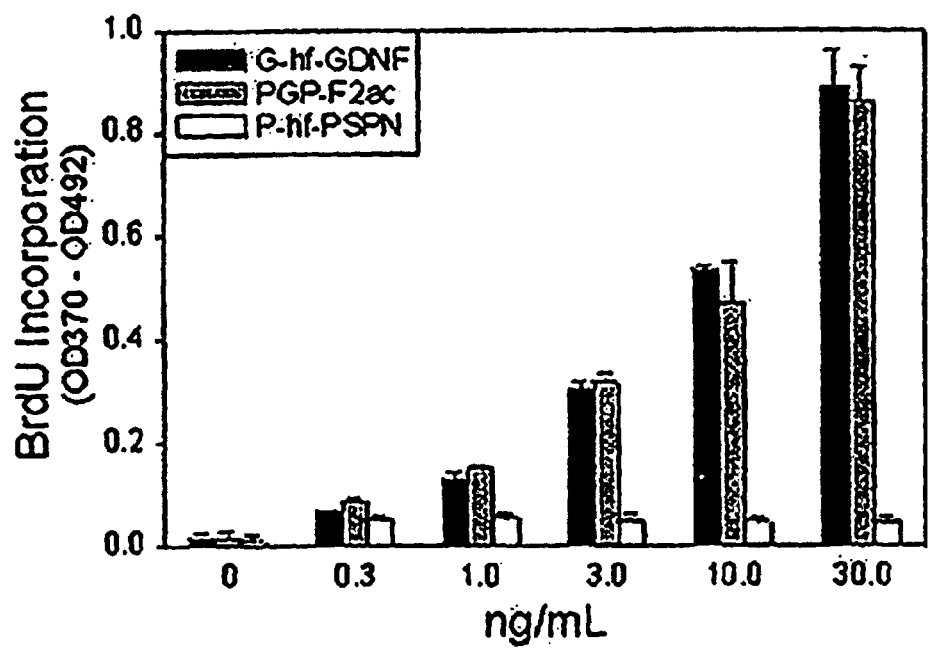
FIG. 5D is a histogram of BrdU incorporation by NBL-S neuroblastoma cells in the presence of the indicated factors purified from conditioned medium of transiently transfected COS cells, showing that mutant PGP-F2ac stimulates proliferation of NBL-S cells at a similar level to GDNF at all doses tested.
Figure 7A:
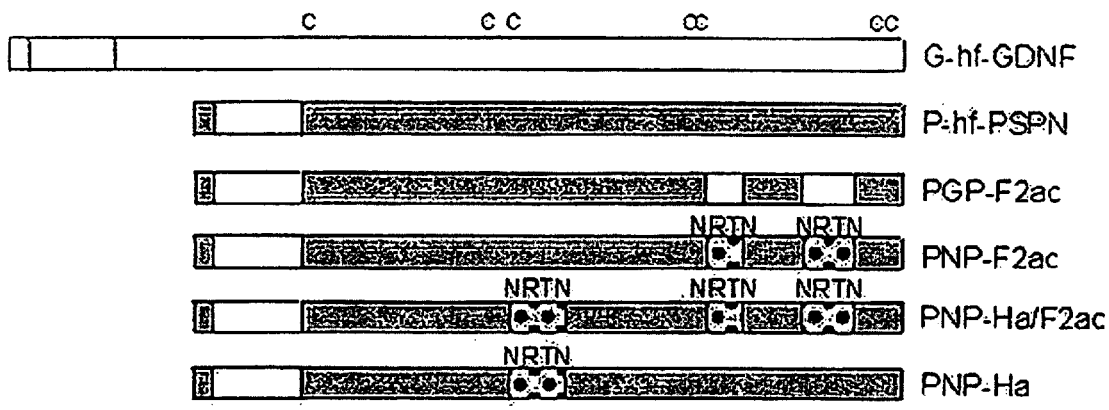
FIG. 7A is a schematic diagram depicting the structures of G-hf-GDNF, P-hf-PSPN, PGP-F2ac, PNP-F2ac, PNP-Ha/F2ac, and PNP-Ha.

The observation that mutants PGP-F2ac and PNP-F2ac cannot activate GFRα2-RET is consistent with the homologue-scanning mutagenesis in Example 2 (FIG. 4), which suggested that regions in addition to F2a and F2c are required for GDNF to activate GFRα2-RET. In particular, mutant PGP-Ha was significantly attenuated in its ability to activate GFRα2-RET (~27%), whereas it showed a minor loss in the ability to activate GFRα1-RET (~80%; FIG. 4). To address whether region Ha contains additional molecular determinants required for activating GFRα2-RET, a persephin mutant was generated with regions F2a, F2c and Ha replaced by the corresponding regions from neurturin, the highest affinity GFRα2 agonist (PNP-Ha/F2ac; FIG. 7A). While mutant PNP-F2ac elicited only a minor increase in GFRα2-RET activation as before, mutant PNP-Ha/F2ac was significantly better at activating GFRα2-RET, however it did not restore full activity (usually 70–80% of GDNF; FIG. 7B). Therefore, consistent with the homologue-scanning mutagenesis above, these data indicate that regions F2a and F2c of GDNF and NRTN are only sufficient to activate GFRα1-RET, and additional regions are required for full activation of GFRα2-RET (region Ha and perhaps others).

Figure 7C:
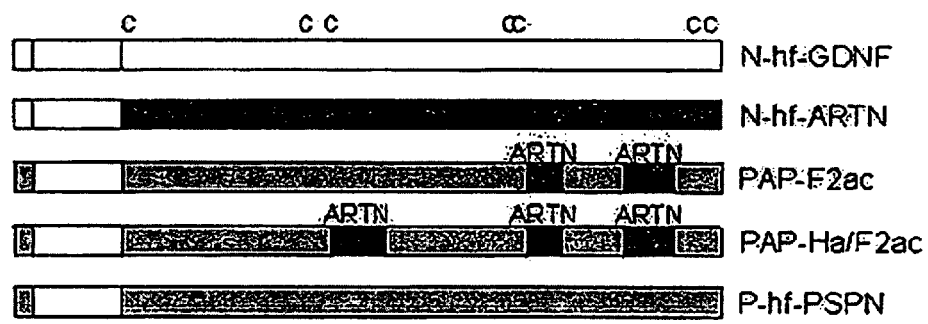
FIG. 7C is a schematic diagram depicting the structures of N-hf-GDNF, N-hf-artemin, PAP-F2ac, PAP-Ha/F2ac, and P-hf-PSPN.
Figure 8A:
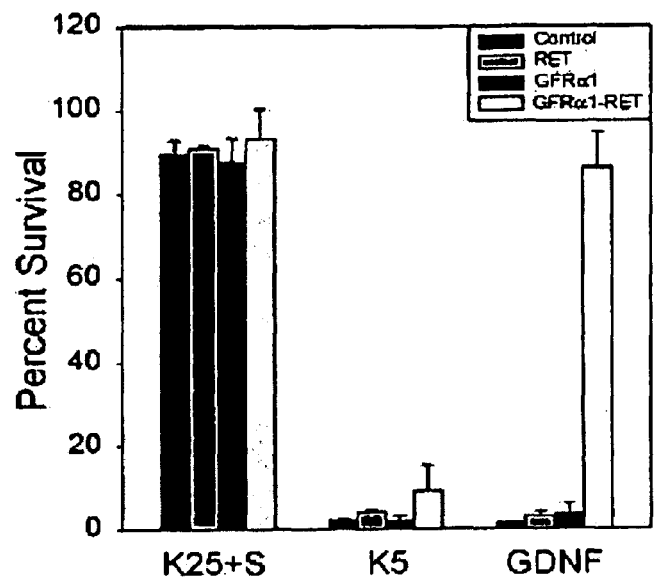
FIG. 8A is a graph showing survival of cerebellar granule cells transfected with the indicated receptor components and cultured for 3 days in the presence of high-potassium plus serum (K25+S), low potassium (K5), or low potassium plus GDNF (GDNF)
Figure 8B:
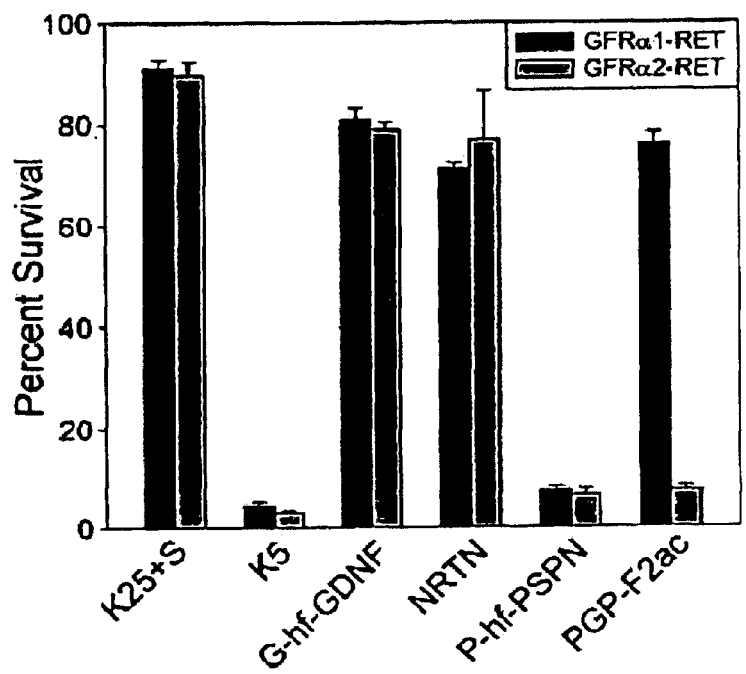
FIG. 8B is a graph showing survival of cerebellar granule cells transfected with GFRα1-RET or GFRα2-RET cultured in the presence of the indicated factors.

Artemin is a recently identified member of the GDNF family ligands that can activate GFRα1-RET, and the only member of the family that can activate GFRα3-RET. As shown in example 3, regions F2a and F2c from artemin are sufficient to activate GFRα1-RET. In an initial attempt to characterize the molecular determinants of the artemin-GFRα3 interaction, the ability of persephin-artemin chimeras to activate the GFRα3-RET receptor complex was examined (FIG. 7C and D). To this end, the chimera N-hf-ARTN was prepared by the fusion PCR mutagenesis procedure as in example 1, where residues 1–13 were truncated from mature human ARTN and attached to the pre-pro region of NRTN the resulting sequence (N- . . . RRAR.PGA-HHHHHHDYKDDDDK-RGCR . . . -C SEQ ID NO. 32). As expected, N-hf-ARTN gave robust activation of GFRα3-RET, whereas N-hf-GDNF showed no activity. Mutant PAP-F2ac, which is capable of activating GFRα1-RET (see FIG. 6), was also unable to activate GFRα3-RET, indicating that like the neurturin-GFRα2 interaction, the artemin-GFRα3 interaction requires regions in addition to F2a and F2c. To determine if region Ha was also involved in the artemin-GFRα3 interaction, a persephin mutant was generated with regions Ha, F2a and F2c from artemin (FIG. 7C). Interestingly, whereas mutant PAP-F2ac was entirely inactive, mutant PAP-Ha/F2ac regained significant activity (ca. 70–80% of full length artemin; FIG. 7D). Therefore, similar to the neurturin-GFRα2 interaction, the artemin-GFRα3 interaction requires molecular determinants from both the heel and finger 2 regions of the molecule, whereas interaction of GDNF, neurturin or artemin with GFRα1 only requires regions F2a and F2c from finger 2.

In this analysis, it was observed that regions F2a and F2c were minimal requirements for interaction with GFRα1-RET, but that additional regions (including region Ha) were required for activating GFRα2-RET. GFRα1-RET is the most promiscuous of the GFL receptors, able to interact with three of the four known ligands. This is consistent with GFRα1-RET having the most minimal requirements for being activated (regions F2a and F2c), and additional regions being required for activating GFRα2-RET and GFRα3-RET. Although region Ha is critical for the neurturin-GFRα2 and artemin-GFRα3 interactions, persephin mutants containing regions Ha, F2a and F2c were not fully active, suggesting either additional regions are necessary, or the binding determinants from neurturin and artemin are not presented properly in the context of the persephin molecule.

EXAMPLE 5

This example illustrates that persephin chimeras which activate GFRα1-RET function as GFRα1-specific agonists in vitro.

The homologue-scanning mutagenesis and gain of function experiments in previous examples demonstrate that for the GFRα1-RET agonists (GDNF, neurturin and artemin), regions F2a and F2c are sufficient for interaction with GFRα1 , but that additional regions are required for interaction with GFRα2 and GFRα3 (FIGS. 6 and 7). This suggests that the persephin mutants containing only regions F2a and F2c from GDNF, neurturin or artemin may function as GFRα1-RET specific agonists.

To test the above idea, a cell survival assay using rat cerebellar granule cells in culture was developed. These cells do not express endogenous RET or GFRα coreceptors and can be transfected efficiently, therefore providing a model system of cell survival with defined receptor components. Rat cerebellar granule cell dissection and culture was performed as described previously Miller and Johnson, *J. Neurosci* 16: 7487–7495, 1996. Timed-pregnant Sprague-Dawley rats were purchased from Harlan Sprague-Dawley (Indianapolis, Ind.). At postnatal day 7 (P7), cerebella were dissected, cut into 1 mm pieces, and incubated for 15 min in 0.3 g/ml trypsin (Worthington, Freehold, N.J.) at 37° C. The pieces were triturated with a fire-polished Pasteur pipette in the presence of trypsin and the resulting cell suspension was passed through a Nitex filter (size 3–20/14; Tetko, Elmsford, N.Y.). Cells were plated at a density of $2.3\times10^5$ cells/$cm^2$ in four-weli dishes (Nunc) coated with 0.1 mg/ml poly-L-lysine. Plating medium (K25+S) consisted of Basal Medium Eagle (Life Tech, Gaithersburg, Md.) containing 10% dialyzed fetal bovine serum, 20 mM KCl, 100 U/ml penicillin and 100 ug/ml streptomycin. To reduce the number of non-neuronal cells, 3.3 μg/ml aphidocholine was added to the medium 24 hrs after plating.

Granule cell transfections were performed using a modified calcium phosphate protocol as described previously (Moulder et al., *J. Neurosci.* 19: 705–715, 1999). Expression plasmids for GFRα1, GFRα2 and RET are described elsewhere (Baloh et al., 1997, supra). At 5 days in vitro (DIV), medium was replaced with Dulbecco's Modified Eagle's Medium (Life Tech) for 1 hr. During this time, an equal volume of solution containing 0.25M CaCl and 67 μg/ml DNA was added to a 2×HEPES-buffered saline [274 mM NaCl, 10 mM KCl, 1.4 mM Na2HPO4-7H2O (Fisher Scientific, Houston, Tex.), 15 mM dextrose, and 42 mM HEPES (free acid), pH 7.07] and incubated in the dark at room temperature for 25 min. 30 μL of the precipitate (1 μg DNA) were added to each of a four-well dish and incubated at 37° C. for 1 hr. Cells were washed twice with Dulbecco's Modified Eagle's Medium and then returned to plating medium. Transfection efficiency was approximately 0.2–0.5%.

To quantify transfection results, the number of initial EGFP-positive cells in a defined area (minimum of 150 cells) of two to four wells (of a four-well dish) per condition were counted 24 hrs after transfection, then rinsed the cultures twice in Dulbecco's Modified Eagle's Medium and switched them to high-potassium/serum (K25+S); low potassium/no serum (K5-S) medium alone; or K5-S supplemented with the indicated factors for 48 hrs. After this period, the number of EGFP-positive cells remaining in the originally defined area of the well was counted again to obtain the percentage neuronal survival.

Cerebellar granule cells transfected with RET or GFRα1 alone do not survive in the absence of high potassium or in the presence of GDNF, however cells cotransfected with GFRα1 and RET survive in the presence of GDNF at levels comparable to the control condition of high potassium plus serum (FIG. 8A; Miller and Johnson, supra). Consistent with other assays, cerebellar granule cells transfected with GFRα1-RET or GFRα2-RET survive in the presence of either GDNF or neurturin, but not persephin (FIG. 8B). However, mutant PGP-F2ac was only capable of supporting the survival of GFRα1-RET transfected, but not GFRα2-RET transfected cells. This is consistent with its minimal ability to activate the GFRα2-RET receptor in fibroblasts (FIG. 6C), and indicates that unlike GDNF and neurturin, mutant PGP-F2ac functions as a GFRα1-RET specific agonist in this in vitro cell survival paradigm.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

All references cited in this specification, including patents and patent applications, are hereby incorporated by reference. The discussion of references herein is intended merely to summarize the assertions made by their authors and no admission is made that any reference constitutes prior art. Applicants reserve the right to challenge the accuracy and pertinence of the cited references.

SUMMARY OF SEQ ID NOS

SEQ ID NO:1—Human Persenhin—C1–C7
CQLWSLTLSVAELGLGYASEEKVIFRYCAGSC-PRGARTQHGLALARLQGQGRAHGGPCCRPTRYT-DVAFLDDRHRWQRLPQLSAAACGC SEQ ID NO:2—Mouse Persephin—C1–C7
CRLWSLTLPVAELGLGYASEEKVIFRYCAGS-CPQEARTQHSLVLARLRGRGRAHGRPCCQPTSY-ADVTFLDDQHHWQQLPQLSAAACGC SEQ ID NO:3—Rat Persephin—C1–C7
CRLWSLTLPVAELGLGYASEEKIIFRYCAGSCPQE-VRTQHSLVLARLRGQGRAHGRPCCQPTSYAD-VTFLDDHHHWQQLPQLSAAACGC SEQ ID NO:4—Human GDNF—C1–C7
CVLTAIHLNVTDLGLGYETKEELIFRYCSGSCD-
   AAETTYDKILKNLSRNRRLVSDKVGQAC-
   CRPIAFDDDLSFLDDNLVYHILRKHSAKRCGC SEQ ID NO:5—Mouse GDNF—C1–C7
CVLTAIHLNVTDLGLGYETKEELIFRYCSGSCESA-
   ETMYDKILKNLSRSRRLTSDKVGQACCR-
   PVAFDDDLSFLDDNLVYHILRKHSAKRCGC SEQ ID NO:6—Rat GDNF—C1–C7
CVLTAIHLNVTDLGLGYETKEELIFRYCSGSCE-
   AAETMYDKILKNLSRSRRLTSDKVGQAC-
   CRPVAFDDDLSFLDDSLVYHILRKHSAKRCGC SEQ ID NO:7—Human Neurtuin—C1–C7
CGLRELEVRVSELGLGYASDETVLFRYCAGACE-
   AAARVYDLGLRRLRQRRRLRRERVRAQP-
   CCRPTAYEDEVSFLDAHSRYHTVHELSARECAC SEQ ID NO:8—Mouse Neurturin—C1–C7
CGLRELEVRVSELGLGYTSDETVLFRYCAGAC-
   EAAIRIYDLGLRRLRQRRRVRRERARAH-
   PCCRPTAYEDEVSFLDVHSRYHTLQELSARECAC SEQ ID NO:9—Human Artemin—C1–C7
CRLRSQLVPVRALGLGHRSDELVRFRFCSGSC-
   RRARSPHDLSLASLLGAGALRPPPGSRPVSQ-
   PCCRPTRYEAVSFMDVNSTWRTVDRLSATACGC SEQ ID NO:10—Mouse Artemin—C1–C7
CRLRSQLVPVSALGLGHSSDELIRFRFCSGSCRRAR-
   SQHDLSLASLLGAGALRSPPGSRPISQPCCRP-
   TRYEAVSFMDVNSTWRTVDHLSATACGC SEQ ID NO:1—His-Flag®-PGP-F2ac (from mouse persephin and rat GDNF): GDNF sequences are underlined
ALAHHHHHHDYKDDDDKGSCRLWSLTLPVAELGLG-
   YASEEKVIFRYCAGSCPQEARTQHSLVLARLRGR-
   GRAHGRPCCQPT<u>AFDDD</u>VTFLDDQHH
   <u>YHILRKH</u>SAAACGC SEQ ID NO:12—PGP-F2ac (from mouse persephin and rat GDNF) C1–C7: GDNF sequences are underlined
CRLWSLTLPVAELGLGYASEEKVIFRYCAGSCPQE-
   ARTQHSLVLARLRGRGRAHGRPCCQPT
   <u>AFDDD</u>VTFLDDQHH<u>YHILRKH</u>SAAACGC SEQ ID NO:13—His-Fla®-PNP-F2ac (from mouse sequences): Neurturin sequences are underlined
ALAHHHHHHDYKDDDDKGSCRLWSLTLPVAELGLG-
   YASEEKVIFRYCAGSCPQEARTQH- SLVLARLRGR-
   GRAHGRPCCQPT<u>AYEDE</u>VTFLDDQHH
   <u>YHTLQEL</u>SAAACGC SEQ ID NO:14—PNP-F2ac (from mouse sequences) C1–C7: Neurturin sequences are underlined
CRLWSLTLPVAEILGLGYASEEKVIFRYCAGSCP-
   QEARTQHSLVLARLRGRGRAHGRPCCQPT
   <u>AYEDE</u>VTFLDDQHH<u>YHTLQEL</u>SAAACGC SEQ ID NO:15—His-Flag®-PAP-F2ac (from mouse sequences): Artemin sequences are underlined
ALAHHHHHHDYKDDDDKGSCRLWSLTLPVAELGLG-
   YASEEKVIEFRYCAGSCPQEARTQHS- LVLARLR-
   GRGRAHGRPCCQPT<u>RYEA</u>VTFLDDQHH
   <u>WRTVDHL</u>SAAACGC SEQ ID NO:16—PAP-F2ac (from mouse sequences) C1–C7: Artemin sequences are underlined
CRLWSLTLPVAELGLGYASEEKVIFRYCAGSCP-
   QEARTQHSLVLARLRGRGRAHGRPCCQPT
   <u>RYEA</u>VTFLDDQHH<u>WRTVDHL</u>SAAACGC SEQ ID NO:17—human GDNF F2a 5-mer
AFDDD SEQ ID NO:18—human neurturin F2a 5-mer
AYEDE SEQ ID NO:19—human artemin F2a 4-mer
RYEA SEQ ID NO:20—human GDNF F2c 7-mer
YHILRKH SEQ ID NO:21—human neurturin F2c 7-mer
YHTVHEL SEQ ID NO:22—human artemin F2c 7-mer
WRTVDRL SEQ ID NO:23—PGP-F2ac (from human sequences) C1–C7: GDNF sequences are underlined
CQLWSLTLSVAELGLGYASEEKVIFRYCAGSCP-
   RGARTQHGLALARLQGQGRAHGGPCCRPT
   <u>AFDDD</u>VAFLDDRHR<u>YHILRKH</u>SAAACGC SEQ ID NO:24—PNP-F2ac (from human sequences) C1–C7: Neurturin sequences are underlined
CQLWSLTLSVAELGLGYASEEKVIFRYCAGSCPR-
   GARTQHGLALARLQGQGRAHGGPCCRPT
   <u>AYEDE</u>VAFLDDRHR<u>YHTVHEL</u>SAAACGC SEQ ID NO:25—PAP-F2ac (from human sequences) C1–C7: Artemin sequences are underlined
CQLWSLTLSVAELGLGYASEEKVIFRYCAGSCPR-
   GARTQHGLALARLQGQGRAHGGPCCRPT
   <u>RYEA</u>VAFLDDRHR<u>WRTVDRL</u>SAAACGC SEQ ID NO:26—full length PGP-F2ac (from human sequences): GDNF sequences are underlined
ALSGPCQLWSLTLSVAELGLGYASEEKVIFRYCAG-
   SCPRGARTQHGLALARLQGQGRAHGGPCCRPT
   <u>AFDDD</u>VAFLDDRHR<u>YHILRKH</u>SAAACGCGG SEQ ID NO:27—full length PNP-F2ac (from human sequences): Neurturin sequences are underlined
ALSGPCQLWSLTLSVAELGLGYASEEKVIFRYCAG-
   SCPRGARTQHGLALARLQGQGRAHGGPCCRPT
   <u>AYEDE</u>VAFLDDRHR<u>YHTVHEL</u>SAAACGCGG SEQ ID NO:28—full length PAP-F2ac (from human sequences): Artemin sequences are underlined
ALSGPCQLWSLTLSVAELGLGYASEEKVIFRYCAG-
   SCPRGARTQHGLALARLQGQGRAHGGPCCRPT
   <u>RYEA</u>VAFLDDRHR<u>WRTVDRL</u>SAAACGCGG SEQ ID NO:29—His-FLAG® mutant G-hf-GDNF
RLKRSPDHHHHHHDYKDDDDKQAAALPRRER-
   NRQAAAASPENSRGKGRRGQRGKNRGCVLTAIHL-
   NVTDLGLGYETKEELIFRYCSGSCEAAETMYD-
   KILKNLSRSRRLTSDKVGQACCRPVAFD-
   DDLSFLDDSLVYHILRKHSAKRCGCI SEQ ID NO:30—His-FLAG® mutant P-hf-PSPN
RLPRALAHHHHHHDYKDDDDKGSCRLWSLTLPVAE-
   LGLGYASEEKVIFRYCAGSCPQEART- QHSLVLAR-
   LRGRGRAHGRPCCQPTSYADVTFLDDQH-
   HWQQLPQLSAAACGCGG SEQ ID NO:31—His-FLAG® mutant N-hf-GDNF
RRARPGAHHHHHHDYKDDDDKRGCVLTAIHL-
   NVTDLGLGYETKEELIFRYCSGSCEAAETMYDKIL-
   KNLSRSRRLTSDKVGQACCRPVAFDDDLSFL-
   DDSLVYHILRKHSAKRCGCI SEQ ID NO:32—amino acid sequence depicting the ligature of human ARTN and NRTN to make His-FLAG® mutant N-hf-ARTN
N- . . . RRARPGAHHHHHHDYKDDDDKRGCR . . . -C

What is claimed is:

1. A polypeptide which activates GFRα1-RET. but does not substantially activate GFRα2-RET or GFRα3-RET, wherein (a) said polypeptide comprises a persephin sequence essentially as set forth in SEQ ID NO: 1, and differing there from only by the presence of substitutions in region F2a (amino acids 60–67 of SEQ ID NO: 1) and substitutions in region F2c (amino acids 77–83 of SEQ ID NO: 1), (b) the substitutions in region F2a comprise from four to eight amino acids that are identical to region F2a of a GDNF family ligand, (c) the substitutions in region F2c comprise from seven to eight amino acids that are identical to region F2c of a GDNF family ligand, (d) the GDNF family ligand is a peptide of SEQ ID NO: 4.

2. The polypeptide of claim 1, wherein the polypeptide comprises a persephin sequence with substitutions for amino acid residues 63–66 of SEQ ID NO:1 selected from the group consisting of SEQ ID NO:17, SEQ ID NO:18 and SEQ ID NO:19, and substitutions for amino acid residues 76–82 of SEQ ID NO:1 selected from the group consisting of SEQ ID NO:20, SEQ ID NO:21 and SEQ ID NO:22.

3. A polypeptide comprising SEQ ID NO:23.

4. The polypeptide of claim 3, consisting of SEQ ID NO:26.

5. A composition comprising the growth factor of claim 3 in a pharmaceutically acceptable preparation.

* * * * *

SEQUENCE LISTING

<160> NUMBER OF SEQ ID NOS: 32

<210> SEQ ID NO 1
<211> LENGTH: 89
<212> TYPE: PRT
<213> ORGANISM: Homo sapiens

<400> SEQUENCE: 1

```
Cys Gln Leu Trp Ser Leu Thr Leu Ser Val Ala Glu Leu Gly Leu Gly
 1               5                  10                  15

Tyr Ala Ser Glu Glu Lys Val Ile Phe Arg Tyr Cys Ala Gly Ser Cys
                20                  25                  30

Pro Arg Gly Ala Arg Thr Gln His Gly Leu Ala Leu Ala Arg Leu Gln
            35                  40                  45

Gly Gln Gly Arg Ala His Gly Gly Pro Cys Cys Arg Pro Thr Arg Tyr
        50                  55                  60

Thr Asp Val Ala Phe Leu Asp Asp Arg His Arg Trp Gln Arg Leu Pro
65                  70                  75                  80

Gln Leu Ser Ala Ala Ala Cys Gly Cys
                85
```

<210> SEQ ID NO 2
<211> LENGTH: 89
<212> TYPE: PRT
<213> ORGANISM: Mouse

<400> SEQUENCE: 2

```
Cys Arg Leu Trp Ser Leu Thr Leu Pro Val Ala Glu Leu Gly Leu Gly
 1               5                  10                  15

Tyr Ala Ser Glu Glu Lys Val Ile Phe Arg Tyr Cys Ala Gly Ser Cys
                20                  25                  30

Pro Gln Glu Ala Arg Thr Gln His Ser Leu Val Leu Ala Arg Leu Arg
            35                  40                  45

Gly Arg Gly Arg Ala His Gly Arg Pro Cys Cys Gln Pro Thr Ser Tyr
        50                  55                  60

Ala Asp Val Thr Phe Leu Asp Asp Gln His His Trp Gln Gln Leu Pro
65                  70                  75                  80

Gln Leu Ser Ala Ala Ala Cys Gly Cys
                85
```

<210> SEQ ID NO 3
<211> LENGTH: 89
<212> TYPE: PRT
<213> ORGANISM: RAT

<400> SEQUENCE: 3

```
Cys Arg Leu Trp Ser Leu Thr Leu Pro Val Ala Glu Leu Gly Leu Gly
 1               5                  10                  15

Tyr Ala Ser Glu Glu Lys Ile Ile Phe Arg Tyr Cys Ala Gly Ser Cys
                20                  25                  30

Pro Gln Glu Val Arg Thr Gln His Ser Leu Val Leu Ala Arg Leu Arg
            35                  40                  45

Gly Gln Gly Arg Ala His Gly Arg Pro Cys Cys Gln Pro Thr Ser Tyr
        50                  55                  60

Ala Asp Val Thr Phe Leu Asp Asp His His Trp Gln Gln Leu Pro
65                  70                  75                  80
```

```
Gln Leu Ser Ala Ala Ala Cys Gly Cys
                85

<210> SEQ ID NO 4
<211> LENGTH: 93
<212> TYPE: PRT
<213> ORGANISM: Homo sapiens

<400> SEQUENCE: 4

Cys Val Leu Thr Ala Ile His Leu Asn Val Thr Asp Leu Gly Leu Gly
  1               5                  10                  15

Tyr Glu Thr Lys Glu Glu Leu Ile Phe Arg Tyr Cys Ser Gly Ser Cys
             20                  25                  30

Asp Ala Ala Glu Thr Thr Tyr Asp Lys Ile Leu Lys Asn Leu Ser Arg
         35                  40                  45

Asn Arg Arg Leu Val Ser Asp Lys Val Gly Gln Ala Cys Cys Arg Pro
     50                  55                  60

Ile Ala Phe Asp Asp Asp Leu Ser Phe Leu Asp Asp Asn Leu Val Tyr
 65                  70                  75                  80

His Ile Leu Arg Lys His Ser Ala Lys Arg Cys Gly Cys
                 85                  90

<210> SEQ ID NO 5
<211> LENGTH: 93
<212> TYPE: PRT
<213> ORGANISM: Mouse

<400> SEQUENCE: 5

Cys Val Leu Thr Ala Ile His Leu Asn Val Thr Asp Leu Gly Leu Gly
  1               5                  10                  15

Tyr Glu Thr Lys Glu Glu Leu Ile Phe Arg Tyr Cys Ser Gly Ser Cys
             20                  25                  30

Glu Ser Ala Glu Thr Met Tyr Asp Lys Ile Leu Lys Asn Leu Ser Arg
         35                  40                  45

Ser Arg Arg Leu Thr Ser Asp Lys Val Gly Gln Ala Cys Cys Arg Pro
     50                  55                  60

Val Ala Phe Asp Asp Asp Leu Ser Phe Leu Asp Asp Asn Leu Val Tyr
 65                  70                  75                  80

His Ile Leu Arg Lys His Ser Ala Lys Arg Cys Gly Cys
                 85                  90

<210> SEQ ID NO 6
<211> LENGTH: 93
<212> TYPE: PRT
<213> ORGANISM: RAT

<400> SEQUENCE: 6

Cys Val Leu Thr Ala Ile His Leu Asn Val Thr Asp Leu Gly Leu Gly
  1               5                  10                  15

Tyr Glu Thr Lys Glu Glu Leu Ile Phe Arg Tyr Cys Ser Gly Ser Cys
             20                  25                  30

Glu Ala Ala Glu Thr Met Tyr Asp Lys Ile Leu Lys Asn Leu Ser Arg
         35                  40                  45

Ser Arg Arg Leu Thr Ser Asp Lys Val Gly Gln Ala Cys Cys Arg Pro
     50                  55                  60

Val Ala Phe Asp Asp Asp Leu Ser Phe Leu Asp Ser Leu Val Tyr
 65                  70                  75                  80

His Ile Leu Arg Lys His Ser Ala Lys Arg Cys Gly Cys
```

<210> SEQ ID NO 7
<211> LENGTH: 94
<212> TYPE: PRT
<213> ORGANISM: Homo sapiens

<400> SEQUENCE: 7

```
Cys Gly Leu Arg Glu Leu Glu Val Arg Val Ser Glu Leu Gly Leu Gly
  1               5                  10                  15

Tyr Ala Ser Asp Glu Thr Val Leu Phe Arg Tyr Cys Ala Gly Ala Cys
             20                  25                  30

Glu Ala Ala Arg Val Tyr Asp Leu Gly Leu Arg Arg Leu Arg Gln
         35                  40                  45

Arg Arg Arg Leu Arg Arg Glu Arg Val Arg Ala Gln Pro Cys Cys Arg
     50                  55                  60

Pro Thr Ala Tyr Glu Asp Glu Val Ser Phe Leu Asp Ala His Ser Arg
 65                  70                  75                  80

Tyr His Thr Val His Glu Leu Ser Ala Arg Glu Cys Ala Cys
                 85                  90
```

<210> SEQ ID NO 8
<211> LENGTH: 94
<212> TYPE: PRT
<213> ORGANISM: Mouse

<400> SEQUENCE: 8

```
Cys Gly Leu Arg Glu Leu Glu Val Arg Val Ser Glu Leu Gly Leu Gly
  1               5                  10                  15

Tyr Thr Ser Asp Glu Thr Val Leu Phe Arg Tyr Cys Ala Gly Ala Cys
             20                  25                  30

Glu Ala Ala Ile Arg Ile Tyr Asp Leu Gly Leu Arg Arg Leu Arg Gln
         35                  40                  45

Arg Arg Arg Val Arg Arg Glu Arg Ala Arg Ala His Pro Cys Cys Arg
     50                  55                  60

Pro Thr Ala Tyr Glu Asp Glu Val Ser Phe Leu Asp Val His Ser Arg
 65                  70                  75                  80

Tyr His Thr Leu Gln Glu Leu Ser Ala Arg Glu Cys Ala Cys
                 85                  90
```

<210> SEQ ID NO 9
<211> LENGTH: 96
<212> TYPE: PRT
<213> ORGANISM: Homo sapiens

<400> SEQUENCE: 9

```
Cys Arg Leu Arg Ser Gln Leu Val Pro Val Arg Ala Leu Gly Leu Gly
  1               5                  10                  15

His Arg Ser Asp Glu Leu Val Arg Phe Arg Phe Cys Ser Gly Ser Cys
             20                  25                  30

Arg Arg Ala Arg Ser Pro His Asp Leu Ser Leu Ala Ser Leu Leu Gly
         35                  40                  45

Ala Gly Ala Leu Arg Pro Pro Pro Gly Ser Arg Pro Val Ser Gln Pro
     50                  55                  60

Cys Cys Arg Pro Thr Arg Tyr Glu Ala Val Ser Phe Met Asp Val Asn
 65                  70                  75                  80

Ser Thr Trp Arg Thr Val Asp Arg Leu Ser Ala Thr Ala Cys Gly Cys
                 85                  90                  95
```

```
<210> SEQ ID NO 10
<211> LENGTH: 96
<212> TYPE: PRT
<213> ORGANISM: Mouse

<400> SEQUENCE: 10

Cys Arg Leu Arg Ser Gln Leu Val Pro Val Ser Ala Leu Gly Leu Gly
 1               5                  10                  15

His Ser Ser Asp Glu Leu Ile Arg Phe Arg Phe Cys Ser Gly Ser Cys
                20                  25                  30

Arg Arg Ala Arg Ser Gln His Asp Leu Ser Leu Ala Ser Leu Leu Gly
            35                  40                  45

Ala Gly Ala Leu Arg Ser Pro Pro Gly Ser Arg Pro Ile Ser Gln Pro
        50                  55                  60

Cys Cys Arg Pro Thr Arg Tyr Glu Ala Val Ser Phe Met Asp Val Asn
 65                 70                  75                  80

Ser Thr Trp Arg Thr Val Asp His Leu Ser Ala Thr Ala Cys Gly Cys
                85                  90                  95

<210> SEQ ID NO 11
<211> LENGTH: 109
<212> TYPE: PRT
<213> ORGANISM: MURINE

<400> SEQUENCE: 11

Ala Leu Ala His His His His His His Asp Tyr Lys Asp Asp Asp Asp
 1               5                  10                  15

Lys Gly Ser Cys Arg Leu Trp Ser Leu Thr Leu Pro Val Ala Glu Leu
                20                  25                  30

Gly Leu Gly Tyr Ala Ser Glu Glu Lys Val Ile Phe Arg Tyr Cys Ala
            35                  40                  45

Gly Ser Cys Pro Gln Glu Ala Arg Thr Gln His Ser Leu Val Leu Ala
        50                  55                  60

Arg Leu Arg Gly Arg Gly Arg Ala His Gly Arg Pro Cys Cys Gln Pro
 65                 70                  75                  80

Thr Ala Phe Asp Asp Val Thr Phe Leu Asp Asp Gln His His Tyr
                85                  90                  95

His Ile Leu Arg Lys His Ser Ala Ala Cys Gly Cys
            100                 105

<210> SEQ ID NO 12
<211> LENGTH: 90
<212> TYPE: PRT
<213> ORGANISM: MURINE

<400> SEQUENCE: 12

Cys Arg Leu Trp Ser Leu Thr Leu Pro Val Ala Glu Leu Gly Leu Gly
 1               5                  10                  15

Tyr Ala Ser Glu Glu Lys Val Ile Phe Arg Tyr Cys Ala Gly Ser Cys
                20                  25                  30

Pro Gln Glu Ala Arg Thr Gln His Ser Leu Val Leu Ala Arg Leu Arg
            35                  40                  45

Gly Arg Gly Arg Ala His Gly Arg Pro Cys Cys Gln Pro Thr Ala Phe
        50                  55                  60

Asp Asp Val Thr Phe Leu Asp Asp Gln His His Tyr His Ile Leu
 65                 70                  75                  80
```

```
Arg Lys His Ser Ala Ala Cys Gly Cys
            85              90

<210> SEQ ID NO 13
<211> LENGTH: 109
<212> TYPE: PRT
<213> ORGANISM: Mouse

<400> SEQUENCE: 13

Ala Leu Ala His His His His His His Asp Tyr Lys Asp Asp Asp Asp
  1               5                  10                  15

Lys Gly Ser Cys Arg Leu Trp Ser Leu Thr Leu Pro Val Ala Glu Leu
                 20                  25                  30

Gly Leu Gly Tyr Ala Ser Glu Glu Lys Val Ile Phe Arg Tyr Cys Ala
             35                  40                  45

Gly Ser Cys Pro Gln Glu Ala Arg Thr Gln His Ser Leu Val Leu Ala
 50                  55                  60

Arg Leu Arg Gly Arg Gly Arg Ala His Gly Arg Pro Cys Cys Gln Pro
 65                  70                  75                  80

Thr Ala Tyr Glu Asp Glu Val Thr Phe Leu Asp Asp Gln His His Tyr
                 85                  90                  95

His Thr Leu Gln Glu Leu Ser Ala Ala Ala Cys Gly Cys
                100                 105

<210> SEQ ID NO 14
<211> LENGTH: 90
<212> TYPE: PRT
<213> ORGANISM: Mouse

<400> SEQUENCE: 14

Cys Arg Leu Trp Ser Leu Thr Leu Pro Val Ala Glu Leu Gly Leu Gly
  1               5                  10                  15

Tyr Ala Ser Glu Glu Lys Val Ile Phe Arg Tyr Cys Ala Gly Ser Cys
                 20                  25                  30

Pro Gln Glu Ala Arg Thr Gln His Ser Leu Val Leu Ala Arg Leu Arg
             35                  40                  45

Gly Arg Gly Arg Ala His Gly Arg Pro Cys Cys Gln Pro Thr Ala Tyr
 50                  55                  60

Glu Asp Glu Val Thr Phe Leu Asp Asp Gln His His Tyr His Thr Leu
 65                  70                  75                  80

Gln Glu Leu Ser Ala Ala Ala Cys Gly Cys
                 85                  90

<210> SEQ ID NO 15
<211> LENGTH: 108
<212> TYPE: PRT
<213> ORGANISM: Mouse

<400> SEQUENCE: 15

Ala Leu Ala His His His His His His Asp Tyr Lys Asp Asp Asp Asp
  1               5                  10                  15

Lys Gly Ser Cys Arg Leu Trp Ser Leu Thr Leu Pro Val Ala Glu Leu
                 20                  25                  30

Gly Leu Gly Tyr Ala Ser Glu Glu Lys Val Ile Phe Arg Tyr Cys Ala
             35                  40                  45

Gly Ser Cys Pro Gln Glu Ala Arg Thr Gln His Ser Leu Val Leu Ala
 50                  55                  60

Arg Leu Arg Gly Arg Gly Arg Ala His Gly Arg Pro Cys Cys Gln Pro
```

```
                65                  70                  75                  80
Thr Arg Tyr Glu Ala Val Thr Phe Leu Asp Asp Gln His His Trp Arg
                        85                  90                  95
Thr Val Asp His Leu Ser Ala Ala Ala Cys Gly Cys
                100                 105
```

<210> SEQ ID NO 16
<211> LENGTH: 89
<212> TYPE: PRT
<213> ORGANISM: Mouse

<400> SEQUENCE: 16

```
Cys Arg Leu Trp Ser Leu Thr Leu Pro Val Ala Glu Leu Gly Leu Gly
  1               5                  10                  15
Tyr Ala Ser Glu Glu Lys Val Ile Phe Arg Tyr Cys Ala Gly Ser Cys
                 20                  25                  30
Pro Gln Glu Ala Arg Thr Gln His Ser Leu Val Leu Ala Arg Leu Arg
             35                  40                  45
Gly Arg Gly Arg Ala His Gly Arg Pro Cys Cys Gln Pro Thr Arg Tyr
     50                  55                  60
Glu Ala Val Thr Phe Leu Asp Asp Gln His His Trp Arg Thr Val Asp
 65                  70                  75                  80
His Leu Ser Ala Ala Ala Cys Gly Cys
                 85
```

<210> SEQ ID NO 17
<211> LENGTH: 5
<212> TYPE: PRT
<213> ORGANISM: Homo sapiens

<400> SEQUENCE: 17

```
Ala Phe Asp Asp Asp
  1               5
```

<210> SEQ ID NO 18
<211> LENGTH: 5
<212> TYPE: PRT
<213> ORGANISM: Homo sapiens

<400> SEQUENCE: 18

```
Ala Tyr Glu Asp Glu
  1               5
```

<210> SEQ ID NO 19
<211> LENGTH: 4
<212> TYPE: PRT
<213> ORGANISM: Homo sapiens

<400> SEQUENCE: 19

```
Arg Tyr Glu Ala
  1
```

<210> SEQ ID NO 20
<211> LENGTH: 7
<212> TYPE: PRT
<213> ORGANISM: Homo sapiens

<400> SEQUENCE: 20

```
Tyr His Ile Leu Arg Lys His
  1               5
```

```
<210> SEQ ID NO 21
<211> LENGTH: 7
<212> TYPE: PRT
<213> ORGANISM: Homo sapiens

<400> SEQUENCE: 21

Tyr His Thr Val His Glu Leu
 1               5

<210> SEQ ID NO 22
<211> LENGTH: 7
<212> TYPE: PRT
<213> ORGANISM: Homo sapiens

<400> SEQUENCE: 22

Trp Arg Thr Val Asp Arg Leu
 1               5

<210> SEQ ID NO 23
<211> LENGTH: 90
<212> TYPE: PRT
<213> ORGANISM: Homo sapiens

<400> SEQUENCE: 23

Cys Gln Leu Trp Ser Leu Thr Leu Ser Val Ala Glu Leu Gly Leu Gly
 1               5                   10                  15

Tyr Ala Ser Glu Glu Lys Val Ile Phe Arg Tyr Cys Ala Gly Ser Cys
                20                  25                  30

Pro Arg Gly Ala Arg Thr Gln His Gly Leu Ala Leu Ala Arg Leu Gln
            35                  40                  45

Gly Gln Gly Arg Ala His Gly Gly Pro Cys Cys Arg Pro Thr Ala Phe
    50                  55                  60

Asp Asp Asp Val Ala Phe Leu Asp Asp Arg His Arg Tyr His Ile Leu
65                  70                  75                  80

Arg Lys His Ser Ala Ala Ala Cys Gly Cys
                85                  90

<210> SEQ ID NO 24
<211> LENGTH: 90
<212> TYPE: PRT
<213> ORGANISM: Homo sapiens

<400> SEQUENCE: 24

Cys Gln Leu Trp Ser Leu Thr Leu Ser Val Ala Glu Leu Gly Leu Gly
 1               5                   10                  15

Tyr Ala Ser Glu Glu Lys Val Ile Phe Arg Tyr Cys Ala Gly Ser Cys
                20                  25                  30

Pro Arg Gly Ala Arg Thr Gln His Gly Leu Ala Leu Ala Arg Leu Gln
            35                  40                  45

Gly Gln Gly Arg Ala His Gly Gly Pro Cys Cys Arg Pro Thr Ala Tyr
    50                  55                  60

Glu Asp Glu Val Ala Phe Leu Asp Asp Arg His Arg Tyr His Thr Val
65                  70                  75                  80

His Glu Leu Ser Ala Ala Ala Cys Gly Cys
                85                  90

<210> SEQ ID NO 25
<211> LENGTH: 89
<212> TYPE: PRT
<213> ORGANISM: Homo sapiens
```

```
<400> SEQUENCE: 25

Cys Gln Leu Trp Ser Leu Thr Leu Ser Val Ala Glu Leu Gly Leu Gly
  1               5                  10                  15

Tyr Ala Ser Glu Glu Lys Val Ile Phe Arg Tyr Cys Ala Gly Ser Cys
             20                  25                  30

Pro Arg Gly Ala Arg Thr Gln His Gly Leu Ala Leu Ala Arg Leu Gln
         35                  40                  45

Gly Gln Gly Arg Ala His Gly Gly Pro Cys Cys Arg Pro Thr Arg Tyr
 50                  55                  60

Glu Ala Val Ala Phe Leu Asp Asp Arg His Arg Trp Arg Thr Val Asp
 65                  70                  75                  80

Arg Leu Ser Ala Ala Ala Cys Gly Cys
                 85

<210> SEQ ID NO 26
<211> LENGTH: 97
<212> TYPE: PRT
<213> ORGANISM: Homo sapiens

<400> SEQUENCE: 26

Ala Leu Ser Gly Pro Cys Gln Leu Trp Ser Leu Thr Leu Ser Val Ala
  1               5                  10                  15

Glu Leu Gly Leu Gly Tyr Ala Ser Glu Glu Lys Val Ile Phe Arg Tyr
             20                  25                  30

Cys Ala Gly Ser Cys Pro Arg Gly Ala Arg Thr Gln His Gly Leu Ala
         35                  40                  45

Leu Ala Arg Leu Gln Gly Gln Gly Arg Ala His Gly Gly Pro Cys Cys
 50                  55                  60

Arg Pro Thr Ala Phe Asp Asp Val Ala Phe Leu Asp Asp Arg His
 65                  70                  75                  80

Arg Tyr His Ile Leu Arg Lys His Ser Ala Ala Cys Gly Cys Gly
                 85                  90                  95

Gly

<210> SEQ ID NO 27
<211> LENGTH: 97
<212> TYPE: PRT
<213> ORGANISM: Homo sapiens

<400> SEQUENCE: 27

Ala Leu Ser Gly Pro Cys Gln Leu Trp Ser Leu Thr Leu Ser Val Ala
  1               5                  10                  15

Glu Leu Gly Leu Gly Tyr Ala Ser Glu Glu Lys Val Ile Phe Arg Tyr
             20                  25                  30

Cys Ala Gly Ser Cys Pro Arg Gly Ala Arg Thr Gln His Gly Leu Ala
         35                  40                  45

Leu Ala Arg Leu Gln Gly Gln Gly Arg Ala His Gly Gly Pro Cys Cys
 50                  55                  60

Arg Pro Thr Ala Tyr Glu Asp Glu Val Ala Phe Leu Asp Asp Arg His
 65                  70                  75                  80

Arg Tyr His Thr Val His Glu Leu Ser Ala Ala Ala Cys Gly Cys Gly
                 85                  90                  95

Gly

<210> SEQ ID NO 28
<211> LENGTH: 96
```

```
<212> TYPE: PRT
<213> ORGANISM: Homo sapiens

<400> SEQUENCE: 28

Ala Leu Ser Gly Pro Cys Gln Leu Trp Ser Leu Thr Leu Ser Val Ala
 1               5                  10                  15

Glu Leu Gly Leu Gly Tyr Ala Ser Glu Glu Lys Val Ile Phe Arg Tyr
             20                  25                  30

Cys Ala Gly Ser Cys Pro Arg Gly Ala Arg Thr Gln His Gly Leu Ala
         35                  40                  45

Leu Ala Arg Leu Gln Gly Gln Gly Arg Ala His Gly Gly Pro Cys Cys
     50                  55                  60

Arg Pro Thr Arg Tyr Glu Ala Val Ala Phe Leu Asp Asp Arg His Arg
 65                  70                  75                  80

Trp Arg Thr Val Asp Arg Leu Ser Ala Ala Cys Gly Cys Gly Gly
                 85                  90                  95

<210> SEQ ID NO 29
<211> LENGTH: 151
<212> TYPE: PRT
<213> ORGANISM: Homo sapiens

<400> SEQUENCE: 29

Arg Leu Lys Arg Ser Pro Asp His His His His His Asp Tyr Lys
 1               5                  10                  15

Asp Asp Asp Asp Lys Gln Ala Ala Ala Leu Pro Arg Arg Glu Arg Asn
             20                  25                  30

Arg Gln Ala Ala Ala Ser Pro Glu Asn Ser Arg Gly Lys Gly Arg
         35                  40                  45

Arg Gly Gln Arg Gly Lys Asn Arg Gly Cys Val Leu Thr Ala Ile His
     50                  55                  60

Leu Asn Val Thr Asp Leu Gly Leu Gly Tyr Glu Thr Lys Glu Glu Leu
 65                  70                  75                  80

Ile Phe Arg Tyr Cys Ser Gly Ser Cys Glu Ala Ala Glu Thr Met Tyr
                 85                  90                  95

Asp Lys Ile Leu Lys Asn Leu Ser Arg Ser Arg Arg Leu Thr Ser Asp
            100                 105                 110

Lys Glu Gly Gln Ala Cys Cys Arg Pro Val Ala Phe Asp Asp Leu
        115                 120                 125

Ser Phe Leu Asp Asp Ser Leu Val Tyr His Ile Leu Arg Lys His Ser
    130                 135                 140

Ala Lys Arg Cys Gly Cys Ile
145                 150

<210> SEQ ID NO 30
<211> LENGTH: 114
<212> TYPE: PRT
<213> ORGANISM: Homo sapiens

<400> SEQUENCE: 30

Arg Leu Pro Arg Ala Leu Ala His His His His His Asp Tyr Lys
 1               5                  10                  15

Asp Asp Asp Asp Lys Gly Ser Cys Arg Leu Trp Ser Leu Thr Leu Pro
             20                  25                  30

Val Ala Glu Leu Gly Leu Gly Tyr Ala Ser Glu Glu Lys Val Ile Phe
         35                  40                  45

Arg Tyr Cys Ala Gly Ser Cys Pro Gln Glu Ala Arg Thr Gln His Ser
```

-continued

```
     50                  55                  60

Leu Val Leu Ala Arg Leu Arg Gly Arg Gly Arg Ala His Gly Arg Pro
 65                  70                  75                  80

Cys Cys Gln Pro Thr Ser Tyr Ala Asp Val Thr Phe Leu Asp Asp Gln
                 85                  90                  95

His His Trp Gln Gln Leu Pro Gln Leu Ser Ala Ala Ala Cys Gly Cys
            100                 105                 110

Gly Gly

<210> SEQ ID NO 31
<211> LENGTH: 118
<212> TYPE: PRT
<213> ORGANISM: Homo sapiens

<400> SEQUENCE: 31

Arg Ala Arg Arg Pro Gly Ala His His His His His His Asp Tyr Lys
                  5                  10                  15

Asp Asp Asp Asp Lys Arg Gly Cys Val Leu Thr Ala Ile His Leu Asn
             20                  25                  30

Val Thr Asp Leu Gly Leu Gly Tyr Glu Thr Lys Glu Glu Leu Ile Phe
         35                  40                  45

Arg Tyr Cys Ser Gly Ser Cys Glu Ala Ala Glu Thr Met Tyr Asp Lys
     50                  55                  60

Ile Leu Lys Asn Leu Ser Arg Ser Arg Arg Leu Thr Ser Asp Lys Val
 65                  70                  75                  80

Gly Gln Ala Cys Cys Arg Pro Val Ala Phe Asp Asp Asp Asp Leu Ser
                 85                  90                  95

Phe Leu Asp Asp Ser Leu Val Tyr His Ile Leu Arg Lys His Ser Ala
            100                 105                 110

Lys Arg Cys Gly Cys Ile
        115

<210> SEQ ID NO 32
<211> LENGTH: 25
<212> TYPE: PRT
<213> ORGANISM: Homo sapiens

<400> SEQUENCE: 32

Arg Arg Ala Arg Pro Gly Ala His His His His His His Asp Tyr Lys
                  5                  10                  15

Asp Asp Asp Asp Lys Arg Gly Cys Arg
             20                  25
```